(12) United States Patent
Freedman et al.

(10) Patent No.: US 11,918,178 B2
(45) Date of Patent: Mar. 5, 2024

(54) DETECTING DEFICIENT COVERAGE IN GASTROENTEROLOGICAL PROCEDURES

(71) Applicant: Verily Life Sciences LLC, South San Francisco, CA (US)

(72) Inventors: Daniel Freedman, Zikhron Yaaqov (IL); Yacob Yochai Blau, Haifa (IL); Liran Katzir, Tel Aviv (IL); Amit Aides, Haifa (IL); Ilan Moshe Shimshoni, Haifa (IL); Ehud Benyamin Rivlin, Haifa (IL); Yossi Matias, Tel Aviv (IL)

(73) Assignee: Verily Life Sciences LLC, South San Francisco, CA (US)

( * ) Notice: Subject to any disclaimer, the term of this patent is extended or adjusted under 35 U.S.C. 154(b) by 454 days.

(21) Appl. No.: 17/187,382

(22) Filed: Feb. 26, 2021

(65) Prior Publication Data
US 2021/0280312 A1 Sep. 9, 2021

Related U.S. Application Data

(60) Provisional application No. 63/059,328, filed on Jul. 31, 2020, provisional application No. 62/986,325, filed on Mar. 6, 2020.

(51) Int. Cl.
*G06T 7/50* (2017.01)
*A61B 1/00* (2006.01)
(Continued)

(52) U.S. Cl.
CPC .......... *A61B 1/000096* (2022.02); *G06T 7/50* (2017.01); *G06V 10/764* (2022.01);
(Continued)

(58) Field of Classification Search
CPC ....... A61B 1/000096; A61B 1/31; G06T 7/50; G06T 2207/10068; G06T 2207/20081;
(Continued)

(56) References Cited

U.S. PATENT DOCUMENTS

2005/0119550 A1 6/2005 Serra et al.
2017/0046833 A1 2/2017 Lurie et al.
(Continued)

FOREIGN PATENT DOCUMENTS

WO 2020245815 A1 12/2020
WO 2021011190 A1 1/2021

OTHER PUBLICATIONS

Freedman, et al., Detecting Deficient Coverage in Colonoscopies, IEEE Transactions on Medical Imaging, Jan. 23, 2020.
(Continued)

*Primary Examiner* — Charlotte M Baker
(74) *Attorney, Agent, or Firm* — Christensen O'Connor Johnson Kindness PLLC

(57) ABSTRACT

The present disclosure is directed towards systems and methods that leverage machine-learned models to decrease the rate at which abnormal sites are missed during a gastroenterological procedure. In particular, the system and methods of the present disclosure can use machine-learning techniques to determine the coverage rate achieved during a gastroenterological procedure. Measuring the coverage rate of the gastroenterological procedure can allow medical professionals to be alerted when the coverage output is deficient and thus allow an additional coverage to be achieved and as a result increase in the detection rate for abnormal sites (e.g., adenoma, polyp, lesion, tumor, etc.) during the gastroenterological procedure.

20 Claims, 12 Drawing Sheets

(51) Int. Cl.
 G06V 10/764 (2022.01)
 G06V 10/82 (2022.01)
 G06V 20/64 (2022.01)
 G16H 30/40 (2018.01)
 G16H 50/20 (2018.01)
(52) U.S. Cl.
 CPC ............ *G06V 10/82* (2022.01); *G06V 20/647* (2022.01); *G16H 30/40* (2018.01); *G16H 50/20* (2018.01); *G06T 2207/10068* (2013.01); *G06T 2207/20081* (2013.01); *G06T 2207/20084* (2013.01); *G06T 2207/30032* (2013.01)
(58) Field of Classification Search
 CPC . G06T 2207/20084; G06T 2207/30032; G06T 2207/10016; G06T 2207/30028; G06T 7/0016; G06V 10/764; G06V 10/82; G06V 20/647; G06V 2201/031; G16H 30/40; G16H 50/20
 USPC ......................................................... 382/128
 See application file for complete search history.

(56) References Cited

U.S. PATENT DOCUMENTS

2020/0074661 A1* 3/2020 Anisimovskiy ...... H04N 13/128
2021/0090226 A1* 3/2021 Rauniyar .............. G06T 3/0012

OTHER PUBLICATIONS

Freedman et al., Detecting Deficient Coverage in Colonoscopies, ARXIV.Org, Cornell University Library, Jan. 23, 2020.

Ma et al., Real-Time 3D Reconstruction of Colonoscopic Surfaces for Determining Missing Regions, Advances in Intelligent Data Analysis, XIX, Oct. 10, 2019.

International Search Report and Written Opinion, dated Jun. 11, 2021, in corresponding International Patent Application No. PCT/2021/020294, 17 pages.

Mahmud, et al., Computer Vision and augmented reality in gastrointestinal endoscopy, Gastroenterology Report, 3 (3), 2015.

Bernal et al., Building up the Future of Colonoscopy—A Synergy between Clinicians and Computer Scientists, InTech, 2015.

Detecting Abnormal Growths in Colorectal Tissue, National Institutes of Health, Advances in Colorectal Cancer Research, Aug. 19, 2015.

Gordon et al., Depth From Videos in the Wild: Unsupervised Monocular Depth Learning from Unknown Cameras, arXiv:1904.04998v1, Apr. 10, 2019.

Khor et al., Augmented and virtual reality in surgery—the digital surgical environment: applications, limitations and legal pitfalls, Annals of Translational Medicine, 2016.

Li et al., A Novel Augmented Reality Navigation System for Endoscopy Sinus and Skull Base Surgery: A Feasibility Study, PLOS ONE, DOI: 10.1371/journal.pone.0146996, Jan. 12, 2016.

Pantelidis, et al., Virtual and Augmented Reality in Medical Education, InTech, 2018.

Riaz, Assisted Analysis of Gastroenterology Images Using Computer Vision Methodologies, http//www.wisdom.weizmann.ac.il, 2012.

Virtual Colonoscopy and Colon Cancer Screening, bocaradiology.com/dev/virtual_colonoscopy.html, 2014.

Virtual Colonoscopy—3D and Quantitative Imaging Laboratory, 2014.

Wells, 3-D Virtual Reality Colonoscopy: Pursuing a Better Path to Colorectal Cancer Prevention, https://www.uscf.edu/news/2016/07/403406/3-d-virtual-reality-colonoscopy-pursuing-better-path-colorectal-cancer, 2016.

* cited by examiner

DETECTING DEFICIENT COVERAGE IN GASTROENTEROLOGICAL PROCEDURES

CROSS REFERENCE TO RELATED APPLICATIONS

This application claims priority to U.S. Provisional Application No. 63/059,328 filed Jul. 31, 2020 and to U.S. Provisional Application No. 62/986,325 filed Mar. 6, 2020, the contents of which are both incorporated herein by reference.

FIELD

The present disclosure relates generally to the use of computer imaging and analysis in the medical field. More particularly, the present disclosure relates to using machine-learning techniques to improve the effectiveness of gastroenterological procedures such as colonoscopies.

BACKGROUND

Colorectal cancer (CRC) is a serious health problem, resulting in an estimated 900K deaths per year; it is the second deadliest cancer in the United States. CRC is different from other leading cancers in that it is preventable. Specifically, polyps, which are small precancerous dwellings in the colon, may be detected and removed before they actually become cancerous.

Endoscopic procedures such as colonoscopies provide an effective way to identify and potentially remove polyps (small precancerous dwellings in the colon) before the polyp becomes cancerous. However, when a colonoscopy is performed, it is possible that the colonoscopy may fail to detect polyps in the colon. One reason that a polyp may not be detected is that the polyp does not appear in the field of view covered by the colonoscopy.

For example, the literature indicates that endoscopists miss on average 22-28% of polyps during colonoscopies, which includes 20-24% of adenomas. (An adenoma is a polyp which has the potential to become cancerous; this is in contrast to a hyperplastic polyp, which is benign.) There is therefore room for improvement in polyp detection during colonoscopies. The importance of these missed polyps can be quantified in terms of the rate of interval CRC, defined as a CRC that is diagnosed within 60 months of a negative colonoscopy. In particular, it is estimated that a 1% increase in the Adenoma Detection Rate (ADR, defined as the fraction of procedures in which a physician discovers at least one polyp) can lead to a 6% decrease in the rate of interval CRC.

It is therefore imperative to decrease the polyp miss-rate during colonoscopies. In particular, given a well-prepped bowel, one example reason why an endoscopist might miss a polyp is that the polyp simply does not appear in the field of view, as the endoscopist has not properly covered the relevant area during the procedure. Therefore, systems and methods for improving coverage during a gastroenterological procedure are needed in the art.

SUMMARY

Aspects and advantages of embodiments of the present disclosure will be set forth in part in the following description, or can be learned from the description, or can be learned through practice of the embodiments.

One example aspect of the present disclosure is directed to a computer-implemented method for determining coverage in gastroenterological procedures. The method includes obtaining, by one or more computing devices, a plurality of images captured by an endoscopic device during a gastroenterological procedure for a patient, wherein the plurality of images depict respective portions of an anatomical structure viewed by the endoscopic device. The method includes processing, by the one or more computing devices using a machine-learned depth estimation model, the plurality of images to obtain a plurality of depth maps respectively for the plurality of images, wherein the depth map obtained for each image describes one or more depths of the respective portions of the anatomical structure from the endoscopic device. The method includes determining, by the one or more computing devices using a machine-learned coverage estimation model, a coverage output of the anatomical structure based on the plurality of depth maps, wherein the coverage output indicates an amount of the anatomical structure which has been depicted by the plurality of images.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which refers to the appended figures, in which.

Figure 1:
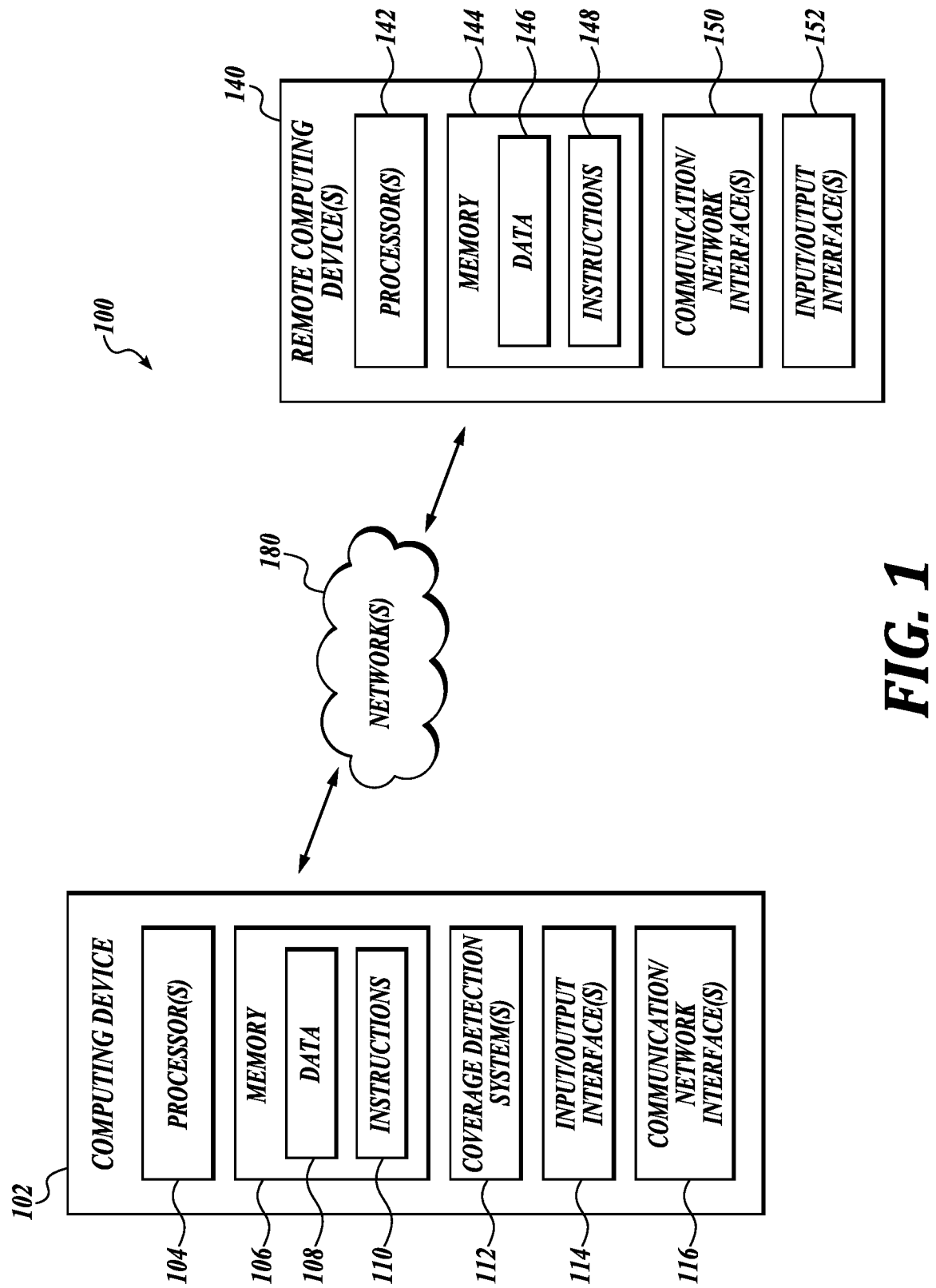
FIG. 1 depicts a block diagram of computing system according to example embodiments of the present disclosure.

Reference numerals that are repeated across plural figures are intended to identify the same features in various implementations.

DETAILED DESCRIPTION

The present disclosure is directed towards systems and methods that leverage machine-learned models to decrease the rate at which abnormal sites are missed during a gastroenterological procedure. In particular, the system and methods of the present disclosure can use machine-learning techniques to determine the coverage rate achieved during a gastroenterological procedure. Measuring the coverage rate of the gastroenterological procedure can allow medical professionals to be alerted when the coverage output is deficient and thus allow an additional coverage to be achieved and as a result increase in the detection rate for abnormal sites (e.g., adenoma, polyp, lesion, tumor, etc.) during the gastroenterological procedure.

In particular, some systems and methods of the present disclosure can operate in two stages to perform coverage computation for gastroenterological procedures such as colonoscopies or other endoscopic procedures. In a first stage, depth estimation of the colon can be performed (e.g., using a machine-learned depth estimation model) given an ordinary RGB video stream; while in the second stage, a coverage can be estimated (e.g., using a machine-learned coverage estimation model) based on the depth estimates generated in the first stage.

In some implementations, the techniques used for depth estimation are based on a deep learning approach, in which a neural network maps images (e.g., RGB images) directly to depth images. One advantage presented by any network-based solution is that it allows for the depth estimation algorithm to run in real-time. However, one example deep learning approach used in some implementations offers two further benefits. First, the approach relies only on unsupervised data; thus, one can learn directly from endoscopic videos without the need for any supervisory signal. Alternative techniques are often based on learning from synthetic data, for which there is depth-supervision; however, this entails the need for domain adaptation, which is avoided in the example approach. Second, the example deep learning approach is calibration-free: it learns the camera intrinsics as part of the algorithm. This is particularly important, as acquiring the intrinsic parameters of a given endoscope is not straightforward; and each endoscopic procedure will use a different endoscope, entailing different parameters.

Given depth estimates produced from the video stream (e.g., using a machine-learned depth estimation model), the proposed systems and methods can then compute coverage, and detect when it is deficient. In some implementations, if deficient coverage is detected (e.g., estimated coverage is found to be below a threshold value), then an alert or alarm can be provided to indicate that the operator of the device should attempt to obtain better coverage before proceeding to a next segment. The alert or alarm can be visual, audio, and/or haptic in nature.

In some implementations, the coverage algorithm is also based on deep learning, but due to the particular character of the problem—that is, the impossibility of ground truth labelling on real colonoscopy sequences—training can be performed on synthetic sequences. However, in the final analysis the coverage algorithm must also work on real sequences. Example implementations of the present disclosure solve the joint requirements of training on synthetic sequences but inference on real sequences through use of a novel two network architecture, with a corresponding two stage training process.

Thus, aspects of the present disclosure provide a novel approach to gastroenterological coverage, which is implemented in some implementations using a two-network architecture with a corresponding two stage training process. Further, the present disclosure provides the first calibration-free unsupervised method for depth estimation applied to colonoscopies. In addition, the combined system is the first coverage system to be evaluated in a large-scale way, and outperforms human experts by a wide margin on coverage tasks, as demonstrated by empirical results contained in the Appendix.

More particularly, a gastroenterological procedure can be performed on a patient using a camera-based medical tool (e.g., a wired or wireless endoscope) which can be inserted into the interior of a patient's body to capture images of a particular structure in the body. For example, during a colonoscopy, an endoscope can be inserted into the patient's body to capture images of the patient's colon. These images can be transmitted to a depth estimation system.

In some examples, the endoscope (whether wired or wireless) can be controlled by a medical professional directly controlling the position and orientation of the endoscope. In other examples, the endoscope can be autonomous (e.g., a robotic endoscope that is controlled by a computer without human intervention) and can use information about the coverage rate to adjust how the endoscope is being controlled. For example, coverage values as generated by the systems described herein can be used as part of a feedback loop for the autonomous or robotic control of the endoscope to ensure sufficient coverage during the procedure. Additionally, or alternatively, the endoscope can use a hybrid control system in which the endoscope can be partially controlled by a computer with a medical professional taking over control as necessary (e.g., when the coverage rate drops).

Due to the lack of supervised training data for depth estimation in the gastroenterological context, aspects of the present disclosure provide a purely unsupervised approach to learn to perform depth estimation, which may be referred to as the view synthesis loss principle.

In particular, the depth estimation system can use each image in the received images as input into a machine-learned depth estimation model. Each frame (e.g., a single image) can be provided as input to the machine-learned depth estimation model. The machine-learned model can be trained to produce a depth image for each frame. A depth image for a particular frame can be a representation of the spatial structure of the frame. For example, a depth image can be a representation of the depth of various portions of the frame (e.g., the distance between a particular portion of the frame and the camera). The depth image can also contain information useful for determining the relative position of different portions of the image to each other.

In some example embodiments, the depth images, once generated, can be transmitted to a pose estimation system. The pose estimation system can use a first frame (a frame associated with time t) and the previous frame (e.g., a frame associated with time t−1) as input to a machine-learned pose estimation model. The pose estimation system can produce a representation of the pose of the current frame. In some examples, a pose can represent the rigid transformation from the current frame (e.g., at time t) to the previous frame (e.g., at time t−1). In some examples, the pose can be expressed as a rotation matrix R and translation vector t.

The process for generating a pose can include generating a point cloud representation of the previous frame based on the depth image of the current frame and the rotation matrix R and the translation vector t. The system can transform each point (e.g., a pixel in the frame) in the point cloud representing the current frame to its corresponding point in the point cloud representing the previous frame, according to the standard formula shown below:

$$z'p' = KRK^{-1}zp + Kt, \quad (1)$$

In the above, p and p' are the original and transformed homogeneous coordinates of the point (e.g., a pixel), respectively; z and z' are the original and transformed depth of the point (e.g., a pixel), respectively; and K is the intrinsic camera matrix:

$$K = \begin{pmatrix} f_x & 0 & x_0 \\ 0 & f_y & y_0 \\ 0 & 0 & 1 \end{pmatrix}. \quad (2)$$

Using the generated point cloud generated for the previous frame, the system can re-render the points using the original color (e.g., RGB) values of the current frame to generate a projected color image for the t−1 frame (which can be labeled $\hat{I}_{t-1}$). Ideally, the depth and pose have been calculated correctly and the projected color image will match the original version of the previous frame (which can be labeled as $I_{t-1}$. The differences between the projected color image and the previous frame can be determined by calculating a difference between the two. The difference (or loss) can be represented by $\delta(I_{t-1}, \hat{I}_{t-1})$, where $\delta$ is some metric between images, e.g. $L_1$. The loss (or difference) can be referred to as the view synthesis loss.

Regarding the image metric $\delta$ between $\hat{I}_{t-1}$ and $I_{t-1}$, the coverage detection system can use two separate metrics: the $L_1$ difference and the structural similarity (SSIM). In addition to RGB consistency, depth consistency is enforced through an L1 penalty on the difference between the warped depth at the source pixel (z') and the native depth at the target frame. The coverage detection system can use the same mechanism to avoid enforcing consistency in areas that become occluded or disoccluded upon transitioning between the two frames.

Once the system has processed one or more frames (e.g., images of a video), the system can calculate which parts of the anatomical structure are visible in the video. The ratio of visible sections of the anatomical structure to structures that are not visible may be referred to as the coverage amount or the coverage rate.

When preparing to calculate the coverage rate of a particular gastroenterological procedure, the system can initialize a three-dimensional model of the anatomical structure. The three-dimensional model of the anatomical structure can include the pair $(\mathcal{M}, s)$ where $\mathcal{M}$ is a 3D mesh forming the surface of the anatomical structure and $s(\cdot)$ is a 3D curve, s: $[0, L] \to \mathbb{R}^3$, traversing the whole anatomical structure, and lying in the center of the anatomical structure. In some examples, the anatomical structure can be a colon and the curve is parameterized by its distance $\ell$ along the curve from the beginning of the colon (rectum). This curve is known as the lumen of the colon.

In some examples, each point m on the mesh $\mathcal{M}$ the closest point to it on the lumen and its corresponding parameter value:

$$\ell*(m) = \ell_{\in [0,L]} \|m - s(\ell)\|$$

Similarly, a given camera position p within the colon can also be associated with its nearest point on the lumen, and for ease of notation, corresponding parameter value is denoted as $\ell*(p)$. For a particular segment of a colonoscopy video, where the initial and final camera positions are $p_0$ and $p_1$, the system can assume that the path of the camera takes is monotonic—that is, the camera is moving from the end of the colon (the cecum) towards the rectum pointing in the direction of the cecum—then the maximal set of points on the colon that can be visible is given by $$\mathcal{V}_{(p_0,p_1)} = \{m \in M : \ell*(p_0) + \Delta_0 \leq \ell*(m) \leq \ell*(p_1) + \Delta_1\}$$

In the above, $\Delta_0$ accounts for the viewing angle of the camera, while $\Delta_1$ accounts for the fact that the image taken from the deepest point on the sequence can view deeper points on the colon. Note that a special case of the coverage can be computed when only a single frame is considered. In this case $p_0 = p_1$, and the system can compute $\mathcal{V}(p_0, p_0)$.

The above computation deals with the maximal set of visible points. In practice, not all points are viewed, and this is what leads to deficient coverage. In particular, given a particular camera position $p \in \mathbb{R}^3$ and orientation $\omega \in \Omega$, the system can define the actual set of points on $\mathcal{M}$ that are visible, which is denoted $\mathcal{A}(p, \omega)$. This is computed by rendering the image given the mesh and the camera pose (position and orientation), given the camera's internal calibration parameters (focal length and principal point); one can then verify which points on $\mathcal{M}$ appear in the rendered image, and these are in the points in $\mathcal{A}(p, \omega)$. Given a full camera trajectory, which is denoted by p: $[0,1] \to \mathbb{R}^3$ and $\omega$: $[0,1] \to \Omega$, the set of actually visible points for the whole trajectory are simply given by $$\mathcal{A}(p(\cdot), \omega(\cdot)) = \bigcup_{t \in [0,1]} \mathcal{A}(p(t), \omega(t))$$

Finally, given a particular camera trajectory $(p(\cdot), \omega(\cdot))$, the coverage is defined as $$C(p(\cdot), \omega(\cdot)) = \frac{\mu[\mathcal{A}(p(\cdot), \omega(\cdot))]}{\mu[\mathcal{V}(p(0), p(1))]}$$

where $\mu$ is the standard measure. Note that in practice, if the vertices on the mesh are sufficiently dense, then one can simply count the vertices in both $\mathcal{A}(p(\cdot), \omega(\cdot))$ and $\mathcal{V}(p(0), p(1))$.

Given the above definition of coverage $C(p(\cdot), \omega(\cdot))$, the system can compute the coverage rate given the video stream produced by the camera trajectory $(p(\cdot), \omega(\cdot))$. The system can use a machine-learned pipeline for computing the coverage. In some examples, the deep learning pipeline (e.g., a machine-learned model) can be trained using supervised learning techniques. For example, the system can use labeled training data to properly train the model.

In some examples, it can be very difficult to label real videos with coverage scores, the coverage detection system can use synthetic videos. Instead, the system uses synthetic videos to accurately train the model. For example, the system can access or generate synthesized videos generated using a rendering engine. Many different trajectories can be generated by taking a base trajectory and adding randomly chosen smooth curves in both the position and orientation of the camera. By generating a variety of trajectories, the computing system can simulate a variety of gastroenterological procedures. Each full simulated procedure can be cut into short segments of 10 seconds or 300 frames.

Once the simulated videos are generated or obtained, the model can be trained in two separate stages. In the first stage, the computing system trains a per-frame network, whose input is a single depth image, and whose output is the visibility for that frame, i.e. $\mathcal{V}(p_0, p_0)$. In some examples, the computing system can use a vector of outputs of several visibilities, each with different viewing angle and look-ahead parameters, corresponding to $\Delta_0$ and $\Delta_1$ above.

In the second stage, the computing system can remove the final layer off of the per-frame network, exposing the penultimate layer which is then taken as a feature vector. The computing system can then train a per-segment coverage network by taking as input the collection of feature vectors, one for each frame in the segment; and the output is the segment coverage $C(p(\bullet), \omega(\bullet))$.

Once all the coverage rate has been determined, a visual representation of the anatomical structure and the coverage rate can be generated and transmitted to a remote system for display. Each depth image can be analyzed for common components and joined together into a single model of the anatomical structure (e.g., the colon of the patient). This can be accomplished by depth image stitching or elastic fusion. The model can then be colored based on the known RGB values from the image data. In some example, the model can be colors such that the covered sections are visually distinct from the sections that are not covered.

The visual representation, along with any captured video data or other data (e.g., medical professional notes) can be transmitted to a remote system for display to a second medical professional, enabling a virtual second opinion. Thus, a second medical professional can review the data produced during the procedure and give feedback to the medical professional performing the procedure.

In some examples, this virtual second opinion can be performed simultaneously (or near simultaneously) with the procedure, such that feedback can be given to a medical professional in real time. In other examples, the video data, virtual representation, and other data, can be saved in a storage system associated with a remote system. Thus, the three-dimensional representation, the coverage map, video data, and any other associated data from the procedure can be accessed at a later date.

According to another aspect, at any point during a gastroenterological procedure (e.g., a colonoscopy), the medical professional performing the gastroenterological procedure can cause a procedure multiview to be enabled. The procedure multiview can enable a virtual reality view of a gastroenterological organ, which may be termed "reconstructed reality." The environment generated can be based on three-dimensional reconstructions of the colon. The reconstructed reality may be performed in a variety of ways, including, for example, the depth estimation techniques described herein.

Once the gastroenterological organ is in the reconstructed reality mode, the medical professional or a second medical professional performing a second opinion may examine the current part of the gastroenterological organ from any angle. This can be particularly relevant in the examination of abnormalities such as polyps and lesions, where geometry can be quite important. It is sometimes difficult to glean the geometry of the object in question from a single view and the medical professional (or a second medical professional providing a virtual second opinion) can get additional information from the reconstructed reality mode.

It is also possible to turn the reconstructed reality mode into an augmented reality mode by overlaying the 3D reconstruction with a number of possible layers. For example, one layer might depict polyps or lesions that have been detected, with colored heatmaps showing their detection probability. Another possible layer might show the classification of the abnormality (for example, polyps can be hyperplastic, adenomatous, or malignant). A third possible layer might color the surface according to the degree that it was viewed in the original pass-through by the medical professional. Other layers are possible as well. Each of these layers can aid enabling a virtual second opinion. The layers can be user-controllable with respect to their presence, opacity, arrangement (e.g., move to back or front, etc.), color, and/or other visual characteristics. Thus, example implementations of the present disclosure can perform real-time and/or post-operative data presentation such as visibility maps, computer-aided design outputs, etc.

Other example aspects are directed to a live and/or post-procedure automated quality/performance report. The live and/or post-procedure automated quality/performance report can provide feedback to a medical professional during and/or after performance of a gastroenterological procedure. The performance report can be visual, textual, and/or audio. The performance report can indicate detections, coverage, and/or other data generated during the procedure. The performance report can be interactive. For example, in some implementations, a user can review 3D imagery to view portions of the gastroenterological organ (e.g., with one or more augmented layers overlaid thereon). The performance report can also indicate a skill or success level of the medical professional. This can provide feedback which may assist the medical professional in improving their skills for future procedures.

The systems and methods of the present disclosure provide a number of technical effects and benefits. As one example, the systems and methods described herein can provide a system for determining whether a given procedure is achieving the expected (or required) coverage rate to ensure that abnormality (e.g., polyp) detection rates are as expected. By ensuring the deficient coverage rates are detected, the systems and methods can provide for improvements in diagnosis accuracy. In addition, because this determination can be performed while a procedure is ongoing, the system can result in significant savings in expenses and time that would be the result if the procedure would need to be repeated. Thus, the system and method disclosed can result in better patient outcomes, reduced cost, and reduced time spent for doctors and their patients.

Additional example technical effects and benefits are enabled by the two-stage approach used in some implementations of the present disclosure. As one example, the two-stage approach enables domain adaptation in which portions of the training are performed on synthetic videos, but the trained system operates to predict coverage on real videos. The concern is that the networks—given their large capacity—may learn some to predict coverage based on some minor artifacts of the synthetic videos which do not then generalize to real videos. The two-stage approach enables domain adaptation, as, in some implementations, the initial per-frame network learns a feature representation based on a rather coarse representation of the 3D geometry, namely the visibility. In example implementations, only this feature vector is then used in the final per-segment network.

Another example technical effect is the ability to train over less training data, which results in savings of computing resources such as processor usage, memory usage, and/or network bandwidth. Synthesizing full videos is a rather heavy operation, as each frame must be rendered, and a video of 5 minutes consists of 9,000 frames. The natural approach, which learns coverage directly from video segments, would require many such segments to converge; and this would necessitate the rendering of a very large number of frames. Using the two-stage approach mitigates this problem: a modest number of video segments, on the order of hundreds, will still consist of many frames. The per-frame network will therefore have a lot of data to learn from (hundreds of thousands of images); whereas the per-segment network will be learning a much easier task and can therefore learn on a considerably smaller amount of data (hundreds of segments) using a network with much lower capacity.

Another example technical effect and benefit is improved inference speed (e.g., reduction in processor usage time or amount) A natural candidate for the architecture of a direct approach is a 3D convolutional neural network; this is the standard architecture that is used in action recognition, for example. Unfortunately, such networks are quite heavy, and cannot generally run in real-time. Other approaches for spatio-temporal data include combined recurrent-convolutional architecture. Example implementations of the present disclosure, by contrast, is a straightforward convolutional architecture and is easy to train.

Another example benefit provided by the present disclosure is the ability to provide a coverage-based performance measure, similar to ADR, by which endoscopists can be graded. The consensus within the field of gastroenterology is that for a procedure to be effective, 90-95% of the colon ought to have been covered. The proposed systems and methods for computing coverage could therefore be used both for alerting the endoscopist to missed regions, as well as for measuring the endoscopist's performance.

Example implementations described herein are the first to be evaluated on a large-scale test set (previous work has tended to perform evaluation on a handful of examples). The Appendix, which is incorporated into and forms a portion of the present disclosure, provides example quantitative performance results on a collection of 561 synthetic sequences. The example results show that on this set, example implementations of the present disclosure outperforms physicians by a factor of 2.4, according to the Mean Average Error (MAE) of coverage. A direct implication of these results is that physicians are not particularly accurate in estimating coverage (they have a high MAE); thus, it may be challenging to use physicians to provide ground truth labels for real sequences. As a result, it may be challenging to quantitatively assess performance on real sequences. Nevertheless, qualitative performance results can be provided on real sequences. While ground truth is not available for such sequences, example implementations of the present disclosure output highly plausible coverage scores that agree with the eyeball test. These results demonstrate the value of the proposed systems: the computation of coverage in general, and detection of deficient coverage in particular, are highly geometric tasks. In such tasks, it is often the case that computers outperform humans, and this is borne out by the example results. In many AI tasks, the goal is simply to do as well as human experts; in the present case, the system outperforms humans, which is of significant value. While the attached Appendix provides examples of how aspects of the present disclosure can be implemented, the present disclosure is not limited to the example implementations contained in the Appendix.

With reference now to the Figures, example embodiments of the present disclosure will be discussed in further detail.

FIG. 1 depicts a block diagram of an example computing system 100 that can facilitate video-based coverage estimation during medical procedures, such as gastroenterological procedures, according to example embodiments of the present disclosure. FIG. 1 illustrates one example computing system 100 that can be used to implement the present disclosure. Other computing systems that include different components can be used in addition or alternatively to the system 100. The system 100 may comprise one or more computing devices, such as computing device 102 and one or more remote computing devices (e.g., server computing systems, etc.), such as remote computing device 130, that are communicatively coupled over one or more networks, such as network 180.

The computing device 102 can be any type of computing device, such as, for example, a personal computing device (e.g., laptop or desktop), a server computing device, or any other type of computing device. The computing device 102 includes one or more processors 104 and one or more memories 106. The one or more processors 104 can be any suitable processing device (e.g., a processor core, a microprocessor, an ASIC, a FPGA, a controller, a microcontroller, etc.) and can be one processor or a plurality of processors that are operatively connected. The memory 106 can include one or more non-transitory computer-readable storage mediums, such as RAM, ROM, EEPROM, EPROM, flash memory devices, magnetic disks, etc., and combinations thereof. The memory 106 can store data 108 and instructions 110 which are executed by the processor 104 to cause the computing device 102 to perform operations, including one or more of the operations disclosed herein.

According to aspects of the present disclosure, the computing device 102 can include one or more systems 112 for detecting a coverage rate for the video captured during a gastroenterological procedure. For example, the computing device 102 can obtain data comprising a video data stream captured by an endoscopic device during a gastroenterological procedure for a patient, and the coverage detection system(s) 112 can determine, based on the video data stream, the amount of coverage for the video data stream (e.g., the percentage of the anatomical structure that is captured by the video data stream).

The coverage detection system 112 can, for each frame of the video data stream, generate a depth image. Each frame (e.g., a single image) is provided as input to the machined learned model. The machine-learned model is trained to produce a depth image for each frame. A depth image for a particular frame can be a representation of the spatial structure of the frame. For example, a depth image can be a representation of the depth of various portions of the frame (e.g., the distance between a particular portion of the frame and the camera). The depth image can also contain information useful for determining the relative position of different portions of the image to each other.

A pose estimation system can be a component of the coverage detection system 112 or can be a distinct component within a larger system. The pose estimation system can use a current frame (a frame captured at time t) and the previous frame (e.g., the frame captured at time t−1) as input to a machine-learned model. The pose estimation system can produce a representation of the pose of the current frame. In some examples, a pose can represent the rigid transformation from the current frame (e.g., at time t) to the previous frame (e.g., at time t−1). In some examples, the pose can be expressed as a rotation matrix R and translation vector t.

The depth image and the pose data can be used to generate a point cloud representation of the previous frame based on the depth image of the current frame and the rotation matrix R and the translation vector t.

The coverage detection system 112 can use the point cloud generated for the previous frame to re-render the points using the original color (e.g., RGB) values of the current frame to generate a projected color image for the t−1 frame (which can be labeled $\hat{I}_{t-1}$). Ideally, the depth and pose have been calculated correctly and the projected color image will match the original version of the previous frame (which can be labeled as $I_{t-1}$. The differences between the projected color image and the previous frame can be determined by calculating a loss. The loss can be represented by $\delta(I_{t-1}, \hat{I}_{t-1})$, where $\delta$ is some metric between images, e.g. $L_1$. The loss (or difference) can be referred to as the view synthesis loss. If the view synthesis exceeds a threshold, the model can be adjusted and the process can be repeated.

The coverage detection system 112 can, using a machine-learned model, generate a coverage rate or coverage amount, for the video data stream. As noted above, the coverage rate can represent the ratio of the points that are visible in the video data stream (or a section of a video data stream) and the number of all possible points that can be viewed in the anatomical structure (or a portion thereof).

The coverage detection system 112 can provide for generating visual presentation(s) of a three-dimensional model of the anatomical structure, the portion of the anatomical structure that is visible in a particular section of video, and the coverage rate. This information can be presented as a visual presentation for use during the procedure or for later analysis during the diagnosis and/or treatment of the patient. Further, in some implementations, the coverage detection system 112 can provide for generating reports of the coverage rate for one or more procedures.

The coverage detection system 112 can include computer logic utilized to provide the desired functionality. The coverage detection system 112 can be implemented in hardware, firmware, and/or software controlling a processor, such as processor 104. For example, in some implementations, the coverage detection system 112 includes program files stored on a storage device, loaded into a memory such as memory 106 and executed by one or more processors such as processor 104. In other implementations, the coverage detection system 112 includes one or more sets of computer-executable instructions that are stored in a tangible computer-readable storage medium such as RAM hard disk or optical or magnetic media.

The computing device 102 can also include one or more input/output interface(s) 114. One or more input/output interface(s) 114 can include, for example, devices for receiving information from or providing information to a user, such as through a display device, touch screen, touchpad, mouse, data entry keys, an audio output device such as one or more speakers, a microphone, haptic feedback device, etc. The computing device 102 can also include one or more communication/network interface(s) 116 used to communicate with one or more systems or devices, including systems or devices that are remotely located from the computing device 102.

In some implementations, the computing device 102 can store or include one or more machine-learned models, such as a depth determination machine-learned model as discussed herein, for example, in association with or included within the coverage detection system 112. For example, the machine-learned models can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Additional machine-learned models include support vector machines, decision-tree based models (e.g., random forests), regression models, and/or other types of models.

The remote computing device 140 can include one or more processors 142 and one or more memories 144. The one or more processors 142 can be any suitable processing device (e.g., a processor core, a microprocessor, an ASIC, a FPGA, a controller, a microcontroller, etc.) and can be one processor or a plurality of processors that are operatively connected. The memory 144 can include one or more non-transitory computer-readable storage mediums, such as RAM, ROM, EEPROM, EPROM, flash memory devices, magnetic disks, etc., and combinations thereof. The memory 144 can store data 146 and instructions 148 which are executed by the processor 142 to cause the remote computing device 140 to perform operations, for example, such as to implement operations as discussed herein. The remote computing device 140 may generate, store, process, and/or the like video data, procedure data, result data, coverage rate data, medical device data, models, and/or the like which can be associated with implementation of one or more operations of the present disclosure, for example, by providing such data to the computing device 102.

In some implementations, the remote computing system 140 includes or is otherwise implemented by one or more server computing devices. In instances in which the remote computing system 140 includes plural server computing devices, such server computing devices can operate according to sequential computing architectures, parallel computing architectures, or some combination thereof.

The remote computing device 140 can also include one or more communication/network interface(s) 150 used to communicate with one or more systems or devices, including systems or devices that are remotely located from the remote computing device 140, such as computing device 102, for example. The remote computing device 140 can also include one or more input/output interface(s) 152, for example, devices for receiving information from or providing information to a user.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

Figure 2:
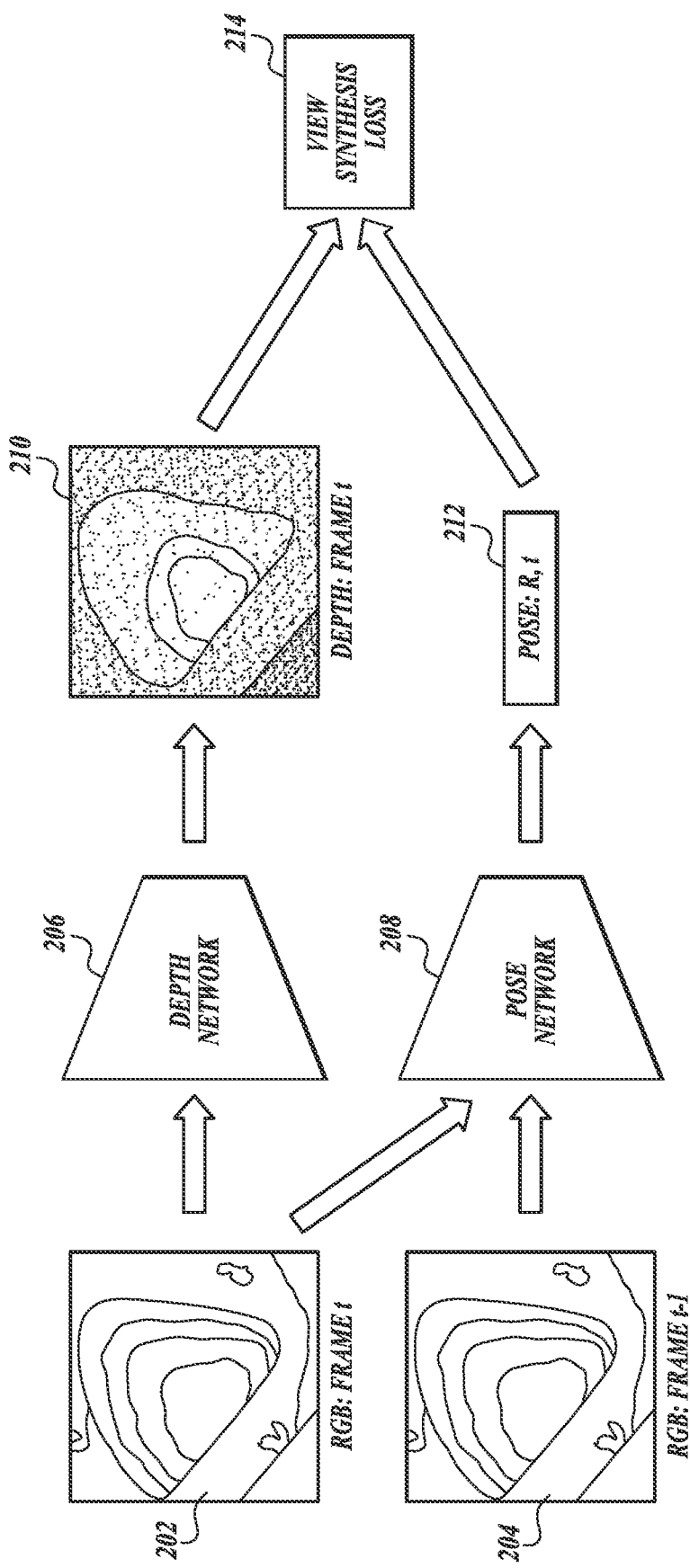
FIG. 2 depicts an example of a diagram of the network architecture for calculating view synthesis loss according to example embodiments of the present disclosure.

FIG. 2 depicts an example of a diagram of a flow for calculating view synthesis loss according to example embodiments of the present disclosure. In some examples, the coverage detection system 112 can include or access a machine-learned model for converting an image (e.g., an RGB image) into a three-dimensional representation that can be used to calculate a coverage rate.

The coverage detection system 112 can access a first frame associated with initial time (t) 202. This frame can be passed to a machine-learned depth network 206. The machine-learned depth network 206 generates, based on the first frame 202, a depth image 210. The depth image 210 can comprise data about the structure of the portion of a colon (or other anatomical structure) in the first frame 202. This information can be represented as a color coding of the distance of each pixel of the first frame 202 from the camera or sensor.

The coverage detection system 112 can access a previous frame 204 associated with time t−1 (e.g., the frame immediately preceding the first frame 202). The first frame 202 and previous frame 204 can be used as input to the pose network 208. In some examples, the depth image can be used as input to the pose network 208.

The coverage detection system 112 can produce a representation of the pose of the first frame 202. In some examples, a pose can represent the rigid transformation from the first frame 202 to the previous frame 204. In some examples, the pose 212 can be expressed as a rotation matrix R and translation vector t.

The depth image and the pose data can be used to generate a point cloud representation of the previous frame based on the depth image of the current frame and the rotation matrix R and the translation vector t.

The coverage detection system 112 can use the generated point cloud generated for the previous frame to re-render the points using the original color (e.g., RGB) values of the current frame to generate a projected color image for the t−1 frame. Ideally, the depth and pose have been calculated correctly and the projected color image will match the original version of the previous frame (which can be labeled as $I_{t-1}$. The differences between the projected color image and the previous frame can be determined by calculating a loss. The loss can be represented by $\delta(I_{t-1}, \hat{I}_{t-1})$, where $\delta$ is some metric between images, e.g. $L_1$. The loss (or difference) can be referred to as the view synthesis loss 214.

Figure 3:
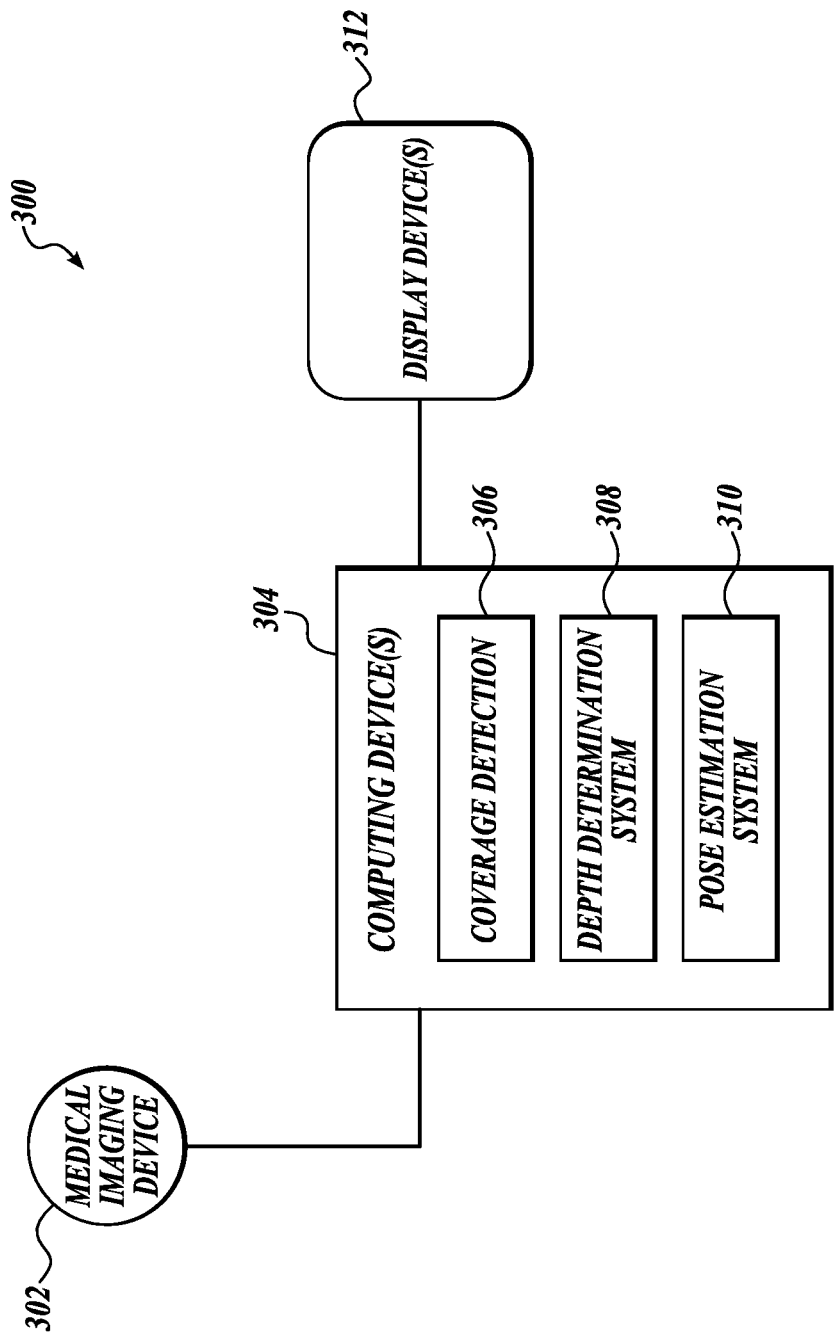
FIG. 3 depicts a block diagram of a system for determining a coverage rate for a video-based procedure according to example embodiments of the present disclosure.

FIG. 3 depicts a block diagram of a system 300 for determining a coverage rate of a video-based procedure according to example embodiments of the present disclosure. According to aspects of the present disclosure, the system 300 can facilitate improvements in the performance of gastroenterological procedures as well as improvements in the overall detection rate and reliability of detection of a gastroenterological procedure. For example, the system for determining a coverage rate for a video-based procedure can analyze captured video data to determine a coverage rate for the gastroenterological procedure.

In some implementations, as illustrated in FIG. 3, a system 300 for determining a coverage rate of a video-based procedure can include a medical imaging device 302 (e.g., an endoscopy system, colonoscopy system, etc.), one or more computing devices 304, and one or more presentation devices 312. The one or more computing devices 304 can include one or more systems to implement one or more of the operations as disclosed herein, which can include a localization-mapping-navigation system 306, an abnormality detection system 308, and a visual presentation generation system 310.

The medical imaging device 302 (e.g., endoscopic device, etc.) can be operated to provide for examination of an anatomical structure of a patient (e.g., colon, small intestine, stomach, other internal organ, etc.) during a gastroenterological procedure. The medical imaging device 302 can generate and provide a video data stream output as the device 302 is guided along a path within the anatomical structure of the patient. The medical imaging device 302 can provide the video data stream as input to the one or more computing devices 304, for example to facilitate determination of the coverage of the current produced via the medical imaging device 302 and increase the likelihood of detection of one or more abnormalities as part of the gastroenterological procedure.

The computing device(s) 304 can perform processing of the video data stream input (e.g., in real-time) to provide for coverage estimation for the medical imaging device 302 (e.g., endoscope, etc.) during the gastroenterological procedure. In some implementations, if deficient coverage is detected (e.g., estimated coverage is found to be below a threshold value), then an alert or alarm can be provided to indicate that the operator of the device should attempt to obtain better coverage before proceeding to a next segment. The alert or alarm can be visual, audio, and/or haptic in nature.

The computing device(s) 304 can include a depth determination system 308. The depth determination system 308 can, through the use of a machine-learned model, generate depth images for one or more frames of a video data stream. The computing device(s) 304 can include a pose estimation system 310. The pose estimation system 310 can use a machine-learned model to estimate a location and position of a camera with respect to the anatomical structure (e.g., a colon).

The computing device(s) 304 can also include a coverage detection system 306. The coverage detection system 306 can determine a coverage rate for a gastroenterological procedure (e.g., a currently occurring gastroenterological procedure or a previously recorded gastroenterological procedure). As noted above, the coverage rate can be a ratio of the points appearing in the video stream data to the total number of possible points.

The computing device(s) 304 can also include a visual presentation generation system that can provide for generating output data based on the gastroenterological procedure. In some implementations, the visual presentation generation system can generate visual presentations that provide indications of the coverage rate, navigation and positioning of the medical imaging device 302, the current viewpoint of the medical imaging device 302, indications of any detected abnormalities (e.g., polyps, lesions, tumors, etc.), indications of the position(s) and/or orientation(s) of detected abnormalities, image data associated with the detected abnormalities, annotation data associated with a detected abnormality generated by the medical imaging device operator (e.g., physician, etc.), and/or the like. The computing device(s) 304 can provide for display of the output generated by the visual presentation generation system, for example, via presentation device(s) 312. The visual presentations generated by the visual presentation generation system can facilitate the diagnosis and/or treatment of the patient (e.g., optical biopsy, surgical determination, future endoscopic procedure, etc.), performance review of the procedure, and/or the like. In some implementations, the output generated by the visual presentation generation system can be displayed, for example via the presentation device(s) 312, in real-time to provide a heads-up type of display to the operator (e.g., physician, etc.) combining different modalities of information in the visual presentation.

The visual presentation generation system can include computer logic utilized to provide desired functionality. The visual presentation generation system can be implemented in hardware, firmware, and/or software controlling a general-purpose processor. For example, in some implementations, the visual presentation generation system includes program files stored on a storage device, loaded into a memory, and executed by one or more processors. In other implementations, the visual presentation generation system includes one or more sets of computer-executable instructions that are stored in a tangible computer-readable storage medium such as RAM hard disk or optical or magnetic media.

Figure 4:
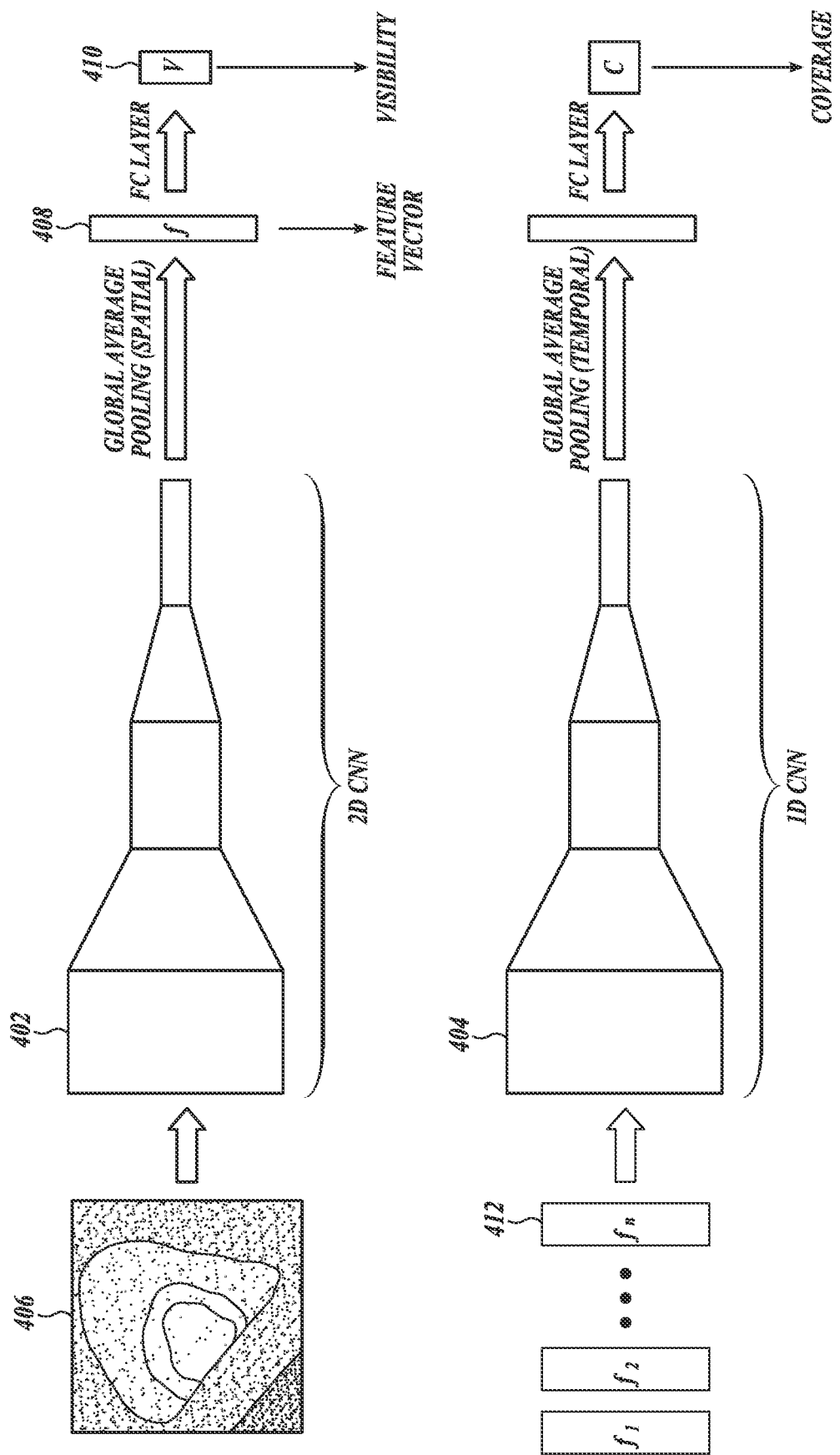
FIG. 4 depicts a diagram of a per-frame network structure according to example embodiments of the present disclosure.

FIG. 4 depicts a diagram of a per-frame and per-segment network structure according to example embodiments of the present disclosure. In some examples, the system can include a per-frame network structure 402 and a per-segment network structure 404.

The input to the per-frame network 402 can be a depth image 406. In some examples, the per-frame network can be a Resnet-50 architecture. The per-frame network can be customized such that the final layer is removed and replaced with a fully connected layer which reduces to a vector 408 of size three. Each entry of this vector 408 can be the visibility 410 computed for different parameters ($\Delta_0$, $\Delta_1$). The per-frame network can be trained with an $L_2$ loss. Once training is complete, the last layer of the per-frame network can be replaced such that the new output (previously, the penultimate layer) is a feature vector of length 2,048.

In some examples, the per-segment network 404 can take segments 412 as input. A segment can be 10 seconds worth of video, which at an example rate of 30 fps translates to 300 frames. Each frame is passed through the per-frame network, yielding a collection of 300 vectors, each of length 2,048. In some examples, this can be a 2-tensor, of length 300, and with 2,048 channels. This 2-tensor is then the input to the network, which is a 1D CNN. This network can be relatively small. In some examples, there are 6 1D convolutional layers, followed by average pooling over the temporal dimension and a final fully-connected layer. The total number of parameters of the network can be 20K, which is quite small.

Figure 5:
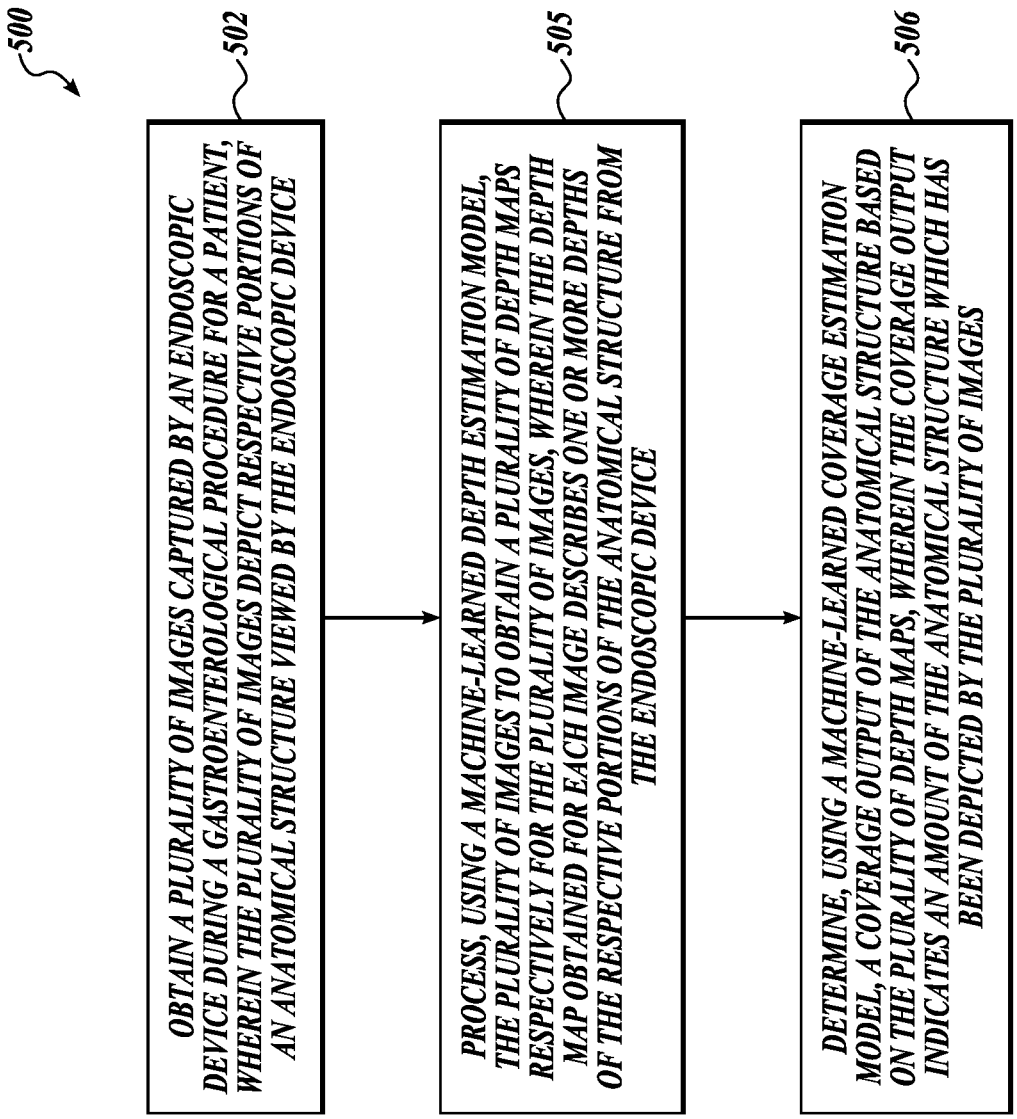
FIG. 5 depicts a flowchart diagram of an example method of determining a coverage rate for gastroenterological procedures according to example embodiments of the present disclosure.

FIG. 5 depicts a flowchart diagram of an example method of determining a coverage rate for gastroenterological procedures according to example embodiments of the present disclosure. Although FIG. 5 depicts steps performed in a particular order for purposes of illustration and discussion, the methods of the present disclosure are not limited to the particularly illustrated order or arrangement. The various steps of the method 400 can be omitted, rearranged, combined, and/or adapted in various ways without deviating from the scope of the present disclosure. Method 500 can be implemented by one or more computing devices, such as one or more of the computing devices depicted in FIGS. 1-4.

At 502, method 500 can include a computing system obtaining a plurality of images captured by an endoscopic device during a gastroenterological procedure for a patient, wherein the plurality of images depict respective portions of an anatomical structure viewed by the endoscopic device. In particular, a medical imaging system (e.g., endoscopy system, etc.) can be operated to provide for an examination of an anatomical structure (e.g., colon, small intestine, stomach, other internal organ or body cavity, etc.) of a patient during a gastroenterological procedure. For example, the medical imaging system can generate a video data stream output (e.g., a series of images), for example, as captured by a camera (e.g., endoscope, WCE, etc.) associated with the medical imaging system as it is navigated within the anatomical structure. The computing system can obtain the plurality of images from the medical imaging system that is generated as part of the gastroenterological procedure.

At 504, method 500 can include a computing system processing, using a machine-learned depth estimation model, the plurality of images to obtain a plurality of depth maps respectively for the plurality of images, wherein the depth map obtained for each image describes one or more depths of the respective portions of the anatomical structure from the endoscopic device. In some examples, the machine-learned depth estimation model has been trained in an unsupervised training scheme using a view synthesis loss function that evaluates a reconstructed image that was reconstructed based on a depth map generated by the machine-learned depth estimation model.

At 506, method 500 can include a computing system determining, by the one or more computing devices using a machine-learned coverage estimation model, a coverage output of the anatomical structure based on the plurality of depth maps, wherein the coverage output indicates an amount of the anatomical structure which has been depicted by the plurality of images.

The amount of the anatomical structure that has been covered can be measured in a variety of ways. For example, the amount of the anatomical structure that has been covered can refer to the ratio of the area of the colon (or other anatomical structure) that have been captured by the image sensor during the procedure relative to the total area the colon that can be captured by the image sensor. Alternatively, the amount of the anatomical structure that has been covered can be measured as a percentage of a currently displayed section of the colon that is visible. For example, the system can calculate what percentage of the current section of a colon is visible relative to the maximum that could be visible with a different camera position or orientation. The amount of the anatomical structure can be an amount of the 3D surface of the structure. Alternatively, the amount of the anatomical structure can be a percentage (or other measure) of a number of most proximate points to such surface on a lumen that traverses through the structure.

In some examples, the amount of the anatomical structure that has been covered can represent what percentage of the whole anatomical structure has been covered, such that as the procedure progresses the percentage will rise. Alternatively, the coverage value can be assessed on a segment-by-segment basis.

In some examples, the computing system generates a visual presentation of the coverage output of the anatomical structure. The computer system provides the visual presentation of the coverage output of the anatomical structure for use in the completion of the gastroenterological procedure or diagnosis of the patient. In some examples, the visual presentation of the coverage output of the anatomical structure is performed in real-time during the gastroenterological procedure. In some examples, the coverage output indicates a percentage of potentially visible portions of the anatomical structure which were depicted by the plurality of images.

In some examples, machine-learned coverage estimation model has been trained in a supervised training scheme using synthetic training data. The machine-learned coverage estimation model comprises a first neural network that is configured to generate, for each depth map, a feature map and a second neural network that is configured to generate, from all feature maps, the coverage output for the gastroenterological procedure. In some examples, the first neural network and the second neural network have been separately trained.

In some examples, the first neural network was trained to generate, from a depth map, a visibility metric indicative of a set of potentially visible points given a particular positioning of the endoscopic device. In some examples, the method is performed for each of a plurality of segments. In some examples, the anatomical structure can comprise a colon and the gastroenterological procedure can comprise a colonoscopy.

Figure 6:
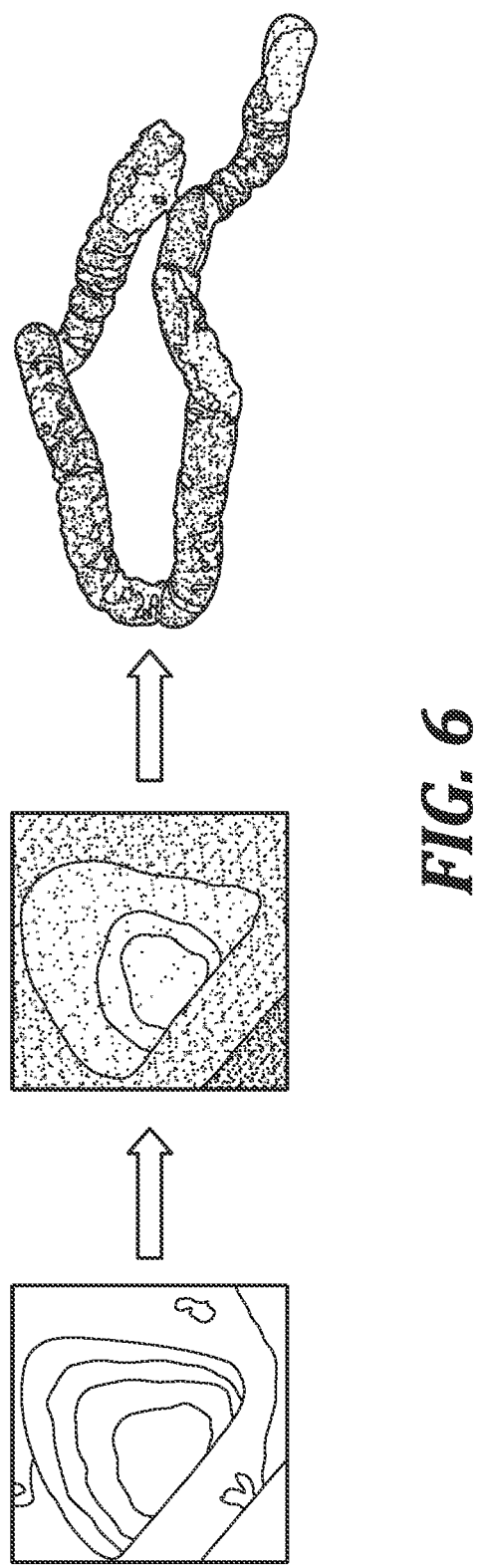
FIG. 6 depicts a process for generating a model of a colon based on captured image data according to example embodiments of the present disclosure.

FIG. 6 depicts a process for generating a model of a colon based on captured image data according to example embodiments of the present disclosure. For example, the system captures a series of images 602. A machine-learned network can generate a depth image for each image in the series of images 602. The system can stitch together a plurality of depth images using any number of possible stitching techniques, one example of which is elastic fusion. The result can be a model of an entire colon.

Figure 7:
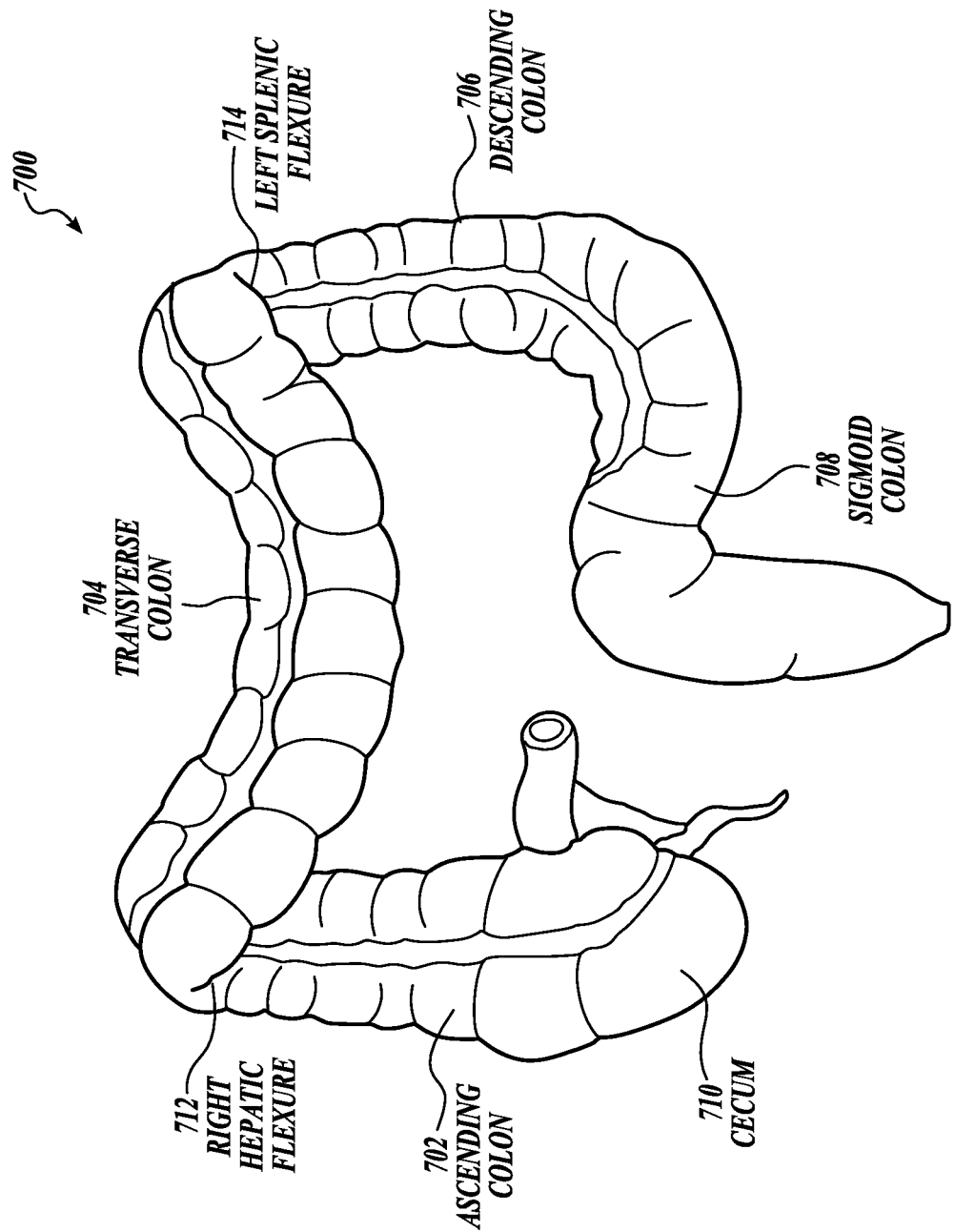
FIG. 7 depicts an example of an anatomical structure in which video-based coverage estimation for gastroenterological procedures may be used according to example embodiments of the present disclosure.

FIG. 7 depicts an example illustration of a model colon 700 in which video-based coverage estimation for a gastroenterological examination procedure may be performed according to example embodiments of the present disclosure. As discussed herein, the fact that an approximate structure of the anatomical structure (e.g., colon, etc.) under examination is known, for example, by using standard atlases of such anatomical structures in generating a three-dimensional model during a gastroenterological procedure.

A human colon, such as model colon 700, includes known structural components that can facilitate the generation of a three-dimensional model of a colon being examined during a gastroenterological procedure and/or identifying landmarks to provide improved positioning, navigation, and detection during a gastroenterological procedure. For example, as illustrated in FIG. 7, model colon 700 comprises the ascending colon 702, the transverse colon 704, the descending colon 706, and the sigmoid colon 708. In addition, a colon includes landmarks, such as the position where the colon twists, such as right hepatic flexure 712 and left splenic flexure 714, that can be easily detected and allow for defining a detected abnormality in relation the landmarks (e.g., defined as the part of the colon between the twists and the distance from the last twist, etc.). Additionally, in some implementations, the detection of important landmarks within an anatomical structure can provide for determination of examination adequacy (e.g., appropriate inspection velocity etc.) as well as provide for later performance review of the gastroenterological procedure.

Figure 8:
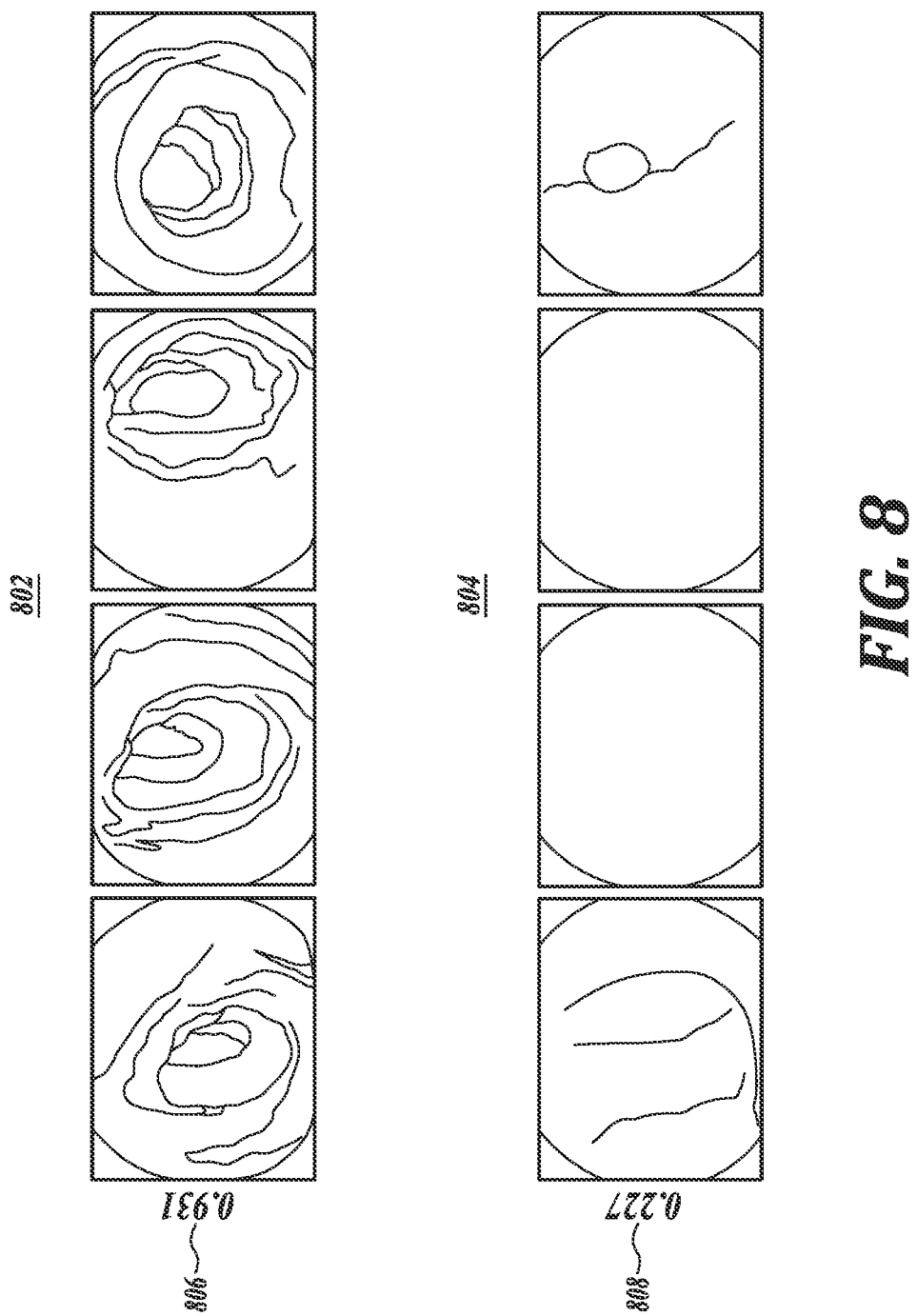
FIG. 8 depicts example detections associated with the performance of video-based coverage estimation for gastroenterological procedures according to example embodiments of the present disclosure.

FIG. 8 depicts an example of a series of images and their associated coverage rate according to example embodiments of the present disclosure. For example, a first series of images 802 includes a series of four images of the interior of a patient's colon. The associated coverage rate 806 is 0.931. This coverage rate represents about 93% coverage of the relevant portions of the colon of the patient.

The second series of images 804 is also a series of four images of the interior of a patient's colon. The coverage rate for the second series of images 804 is 0227, significantly lower than the coverage rate associated with the first series of images. Based on this analysis a user (e.g., a medical professional) can be alerted that better coverage is needed for the second case.

Figure 9:
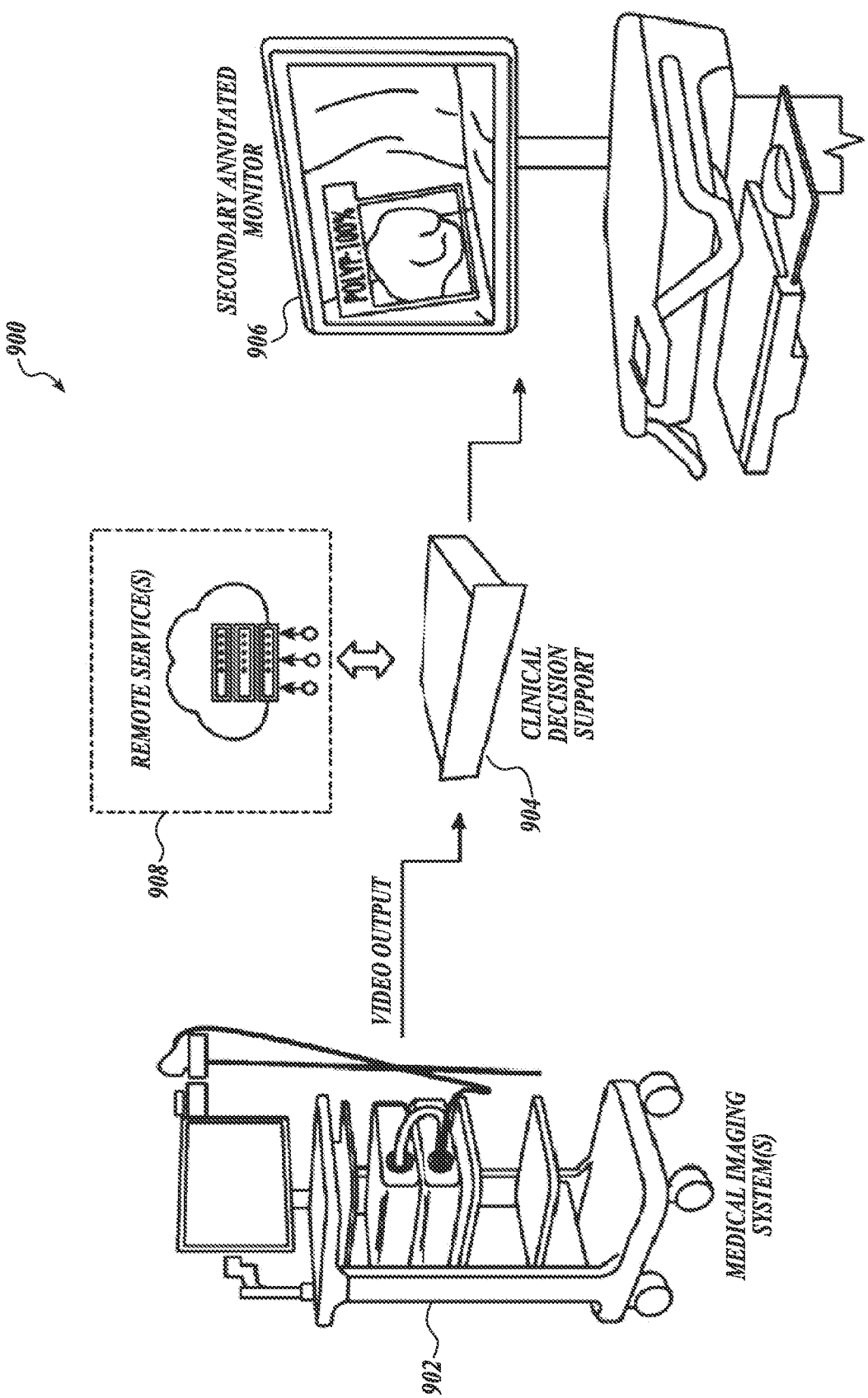
FIG. 9 depicts an example of a system for video-based review of a gastroenterological procedure according to example embodiments of the present disclosure.

FIG. 9 depicts an example of a system 900 for video-based review of a gastroenterological procedure according to example embodiments of the present disclosure. In some implementations, the system 900 for video-based review of a gastroenterological procedure can provide for improvements in detection of abnormalities (e.g., polyps, lesions, tumors, etc.) and/or procedure coverage by allowing a virtual second opinion of the data produced by the procedure (e.g., video and three-dimensional reconstructions) such as video signal data from an endoscopic device during a gastroenterological procedure. As illustrated in FIG. 9, in some implementations, the system 900 can include one or more medical imaging systems 902 (e.g., endoscopy systems, colonoscopy systems, etc.), a clinical support system 904, and a secondary presentation system 906. Additionally, in some implementations, the system 900 can include one or more remote services 908 (e.g., remote server computing systems, cloud-based services, etc.) that can communicate with the clinical support system 904 to facilitate a virtual second opinion of one or more operations such as disclosed below.

The medical imaging system(s) 902 (e.g., endoscopic device, etc.) can be operated to provide for examination of an anatomical structure (e.g., colon, small intestine, stomach, other internal organ or body cavity, etc.) of a patient during a gastroenterological procedure. The medical imaging system(s) 902 can provide a video data stream output, for example, captured by a camera (e.g., endoscope, WCE, etc.) associated with the medical imaging system, as it is guided along a path within the anatomical structure. The medical imaging system(s) 902 can provide the video data stream as input to the clinical support system 904 for use in detection of abnormalities as part of the gastroenterological procedure.

The clinical support system 904 can perform real time processing of the video data stream input to provide for positioning and navigation of a camera of the medical imaging system 902 (e.g., endoscope, WCE, etc.) during the gastroenterological procedure. For example, according to aspects of the present disclosure, real time processing of the video data stream input (e.g., from an endoscope, WCE, etc.) can enable more precise localization, positioning, and navigation of an endoscopic device during a patient gastroenterological procedure, thereby improving procedure coverage and detection rates and providing for the generation of visual presentations of procedure data, such as presentations of the anatomical structure (e.g., colon, small intestine, stomach, other internal organ, etc.), along with positions of any detected abnormalities (e.g., polyps, lesions, tumors, etc.).

The clinical support system 904 can provide for generation of a three-dimensional model of the anatomical structure (e.g., colon, small intestine, stomach, other internal organ, etc.) being examined and determination of the position of the camera (e.g., endoscope, WCE, etc.) in the anatomical structure at all times during the gastroenterological procedure. For example, in some implementations, a clinical support system 904 can perform simultaneous localization and mapping (SLAM) using the video data stream obtained from the medical imaging system 902 during the gastroenterological procedure. Using SLAM, the clinical support system 904 can generate and/or update a three-dimensional model of portions of the anatomical structure (e.g., colon, small intestine, stomach, other internal organ, etc.) of the patient viewed by the camera of the medical imaging system 902 (e.g., endoscope, etc.) as well as determine position/orientation data associated with any abnormalities (e.g., polyps, lesions, tumors, etc.) detected during the gastroenterological procedure. This information can be used to understand and then visualize or otherwise inform a medical professional of procedure coverage (e.g., which portions of the organ have been viewed and which have not yet been viewed).

The clinical support system 904 can provide for detection of abnormalities (e.g., polyps, lesions, tumors, etc.) during the gastroenterological procedure, for example, through the use of machine-learned models that have been trained to generate abnormality detection and/or re-detection probabilities during a gastroenterological procedure.

The clinical support system 904 can provide for generating output including visual representations, for example, based on the three-dimensional model, that can provide indications of the position(s) and/or orientation(s) of detected abnormalities (e.g., in association with the three-dimensional model, etc.), captured image data of the detected abnormalities, and/or the like, for example, for display via the secondary presentation system 906. Visual indications of coverage may also be provided. In some implementations, the visual presentations output can further include operator (e.g., physician) generated notes made during the examination associated with each detected abnormality. The visual presentations can facilitate the diagnosis and/or treatment of the patient, performance review, and/or the like (e.g., optical biopsy, surgical determination, future endoscopic procedure, etc.). In some implementations, the visual presentation of the anatomical structure model, current position/viewpoint of the camera associated with the medical imaging system 902 (e.g., endoscope, etc.) and/or detected abnormality can be displayed by the secondary presentation system 906 in real-time, for example, to provide a heads-up display to the operator (e.g., physician, etc.) and combining different modalities of information in the visual presentation.

Additionally, in some implementations, the clinical support system 904 can provide for generation of a visibility map associated with the anatomical structure (e.g., colon, small intestine, stomach, other internal organ, etc.) being examined. By reconstructing the local three-dimensional structure, a visibility map can be generated and presented to the operator (e.g., physician, etc.), for example, via the secondary presentation system 906. The visibility map can provide a visual overlay of unviewed areas and/or suboptimally exposed areas based on the local three-dimensional structure, thus drawing operator attention (e.g., in real-time) to areas in need of further examination, thereby potentially improving the detection rate of the overall procedure.

In some implementations, the clinical support system 904 can provide for detection and mitigation of device looping during the gastroenterological procedure. For example, by extracting the precise location and pose of the tip of the camera associated with the medical imaging system 902 (e.g., endoscope, etc.) during the gastroenterological procedure can allow for identification of potential looping of the scope shaft and adjustments in guiding the scope to avoid such looping. By providing for mitigating looping of the scope shaft, the clinical support system 904 can help to avoid extended procedure times, incomplete examinations, and/or damage to the anatomical structure under examination (e.g., perforation of the colon wall, etc.).

Additionally, in some implementations, the clinical support system 904 can facilitate performance review and/or the like of a gastroenterological procedure. For example, the clinical support system 904 can generate output data to provide for review of the navigation of an the camera associated with the medical imaging system 902 (e.g., endoscope, etc.) during the gastroenterological procedure, such as to review local navigation relative to landmarks to review completeness and accuracy, to determine velocity of the camera during a procedure (e.g., determining if moving too quickly, etc.), and/or the like. For example, in some implementations, the clinical support system 904 can provide for generating reports of per-procedure performance and quality data. As one example, per-procedure performance and quality data reports can indicate whether a procedure was executed adequately (e.g., quality, coverage, patient discomfort level, etc.), what abnormalities were detected along with positions of such detections (e.g., illustrated on representation of an anatomical structure model), image data associated with any detected abnormalities, annotations generated by the operator (e.g., physician, etc.) during the procedure, and/or the like. Any and all data can be stored, transmitted, or otherwise handled according to appropriate procedures to ensure patient confidentiality.

Additionally, in some embodiments, the system 900 can include one or more remote services 908 (e.g., remote server computing systems, cloud-based services, etc.) that can communicate with the clinical support system 904 to facilitate a second opinion review of a gastrointestinal procedure. In some examples, the second opinion review can be conducted live, at the time that the gastrointestinal procedure is performed. Alternatively, or additionally, the data produced by the clinical support system can be transmitted to the one or more remote services and stored for later review. For example, the clinical support system can produce, as a supplement to the video produced, a three dimensional model that can provide indications of the position(s) and/or orientation(s) of detected abnormalities (e.g., in association with the three-dimensional model, etc.) within the organ, captured image data of the detected abnormalities within the organ, coverage indications, and/or the like, for example, for display to a second opinion reviewer. The second opinion reviewer can include another medical professional, the current medical professional reviewing at a later date, or a software-based evaluation system. In addition, or alternatively, the data produced can include a layer of information intended to be superimposed on video data or on the three-dimensional model that can include information from additional analysis systems (e.g., machine-learned model(s) which facilitate detection of abnormalities) notes from medical professionals, and so on.

Figure 10:
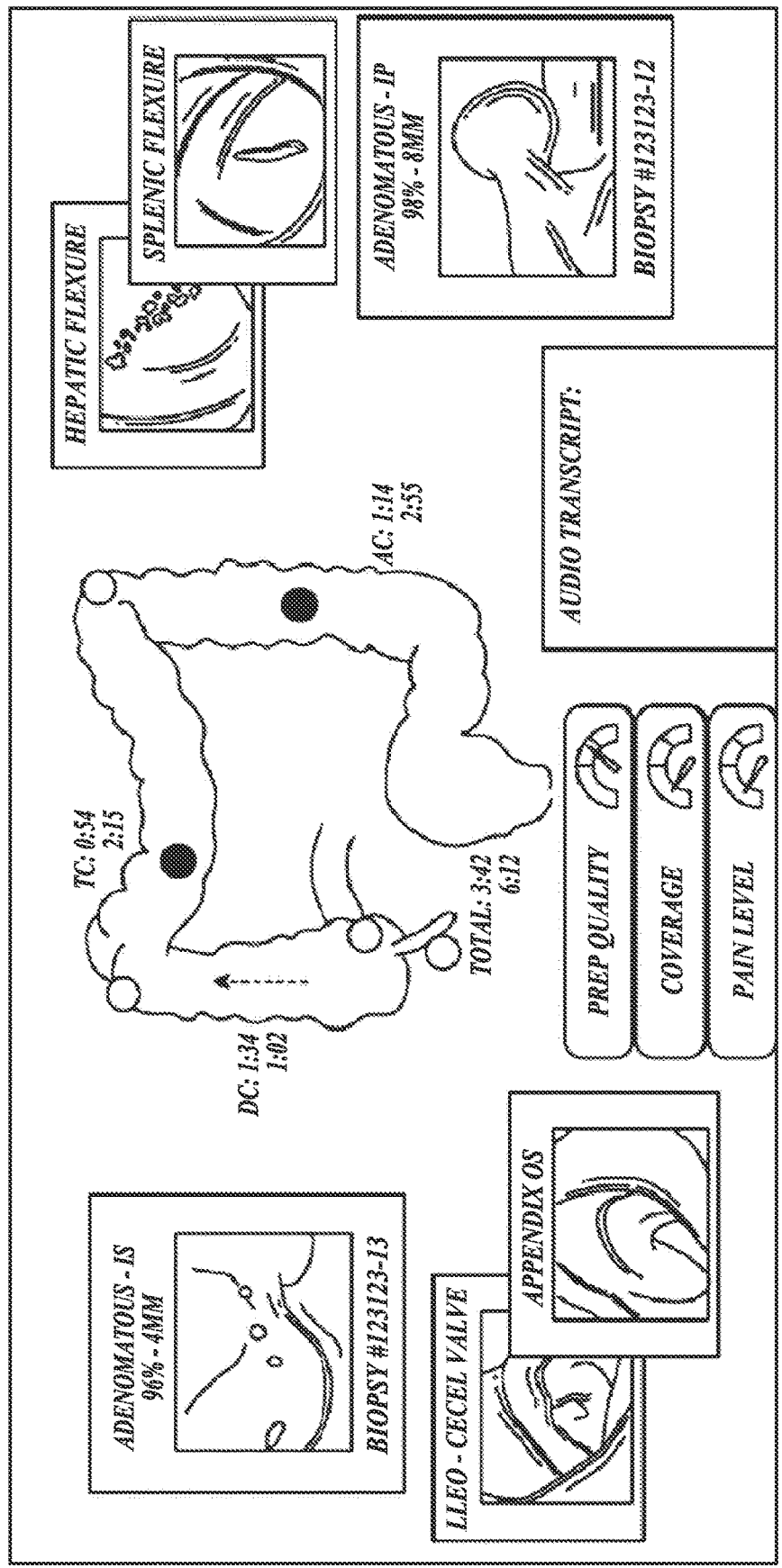
FIG. 10 depicts an example report output provided based on performance of a gastroenterological procedure according to example embodiments of the present disclosure.

FIG. 10 depicts an example report output 1000 provided based on performance of video-based positioning and navigation for a gastroenterological procedure according to example embodiments of the present disclosure. As discussed herein, a computing system (e.g., as illustrated in FIGS. 1 and 9, etc.) can generate performance and quality reporting data, such as performance report 1000, based on data generated during performance of video-based positioning and navigation during a gastroenterological procedure. For example, as illustrated in FIG. 10, a computing system can generate reporting data to provide for diagnosis based on a gastroenterological procedure, provide for performance review of a gastroenterological procedure, and/or the like. For instance, performance report 1000 illustrates an example procedure performance and quality data output associated with a gastroenterological procedure. As an example, in some implementations, a per-procedure performance and quality report, such as report 1000, can indicate whether a procedure was executed adequately (e.g., based on preparation quality measures, procedure coverage measures/results, patient discomfort/pain level measures, etc.), what abnormalities (e.g., polyps, lesions, tumors, etc.) were detected along with positions of such detections (e.g., illustrated on a representation of the anatomical structure), image data associated with detected abnormalities, annotations generated by the device operator (e.g., physician) during the procedure, visibility maps, and/or the like.

Figure 11:
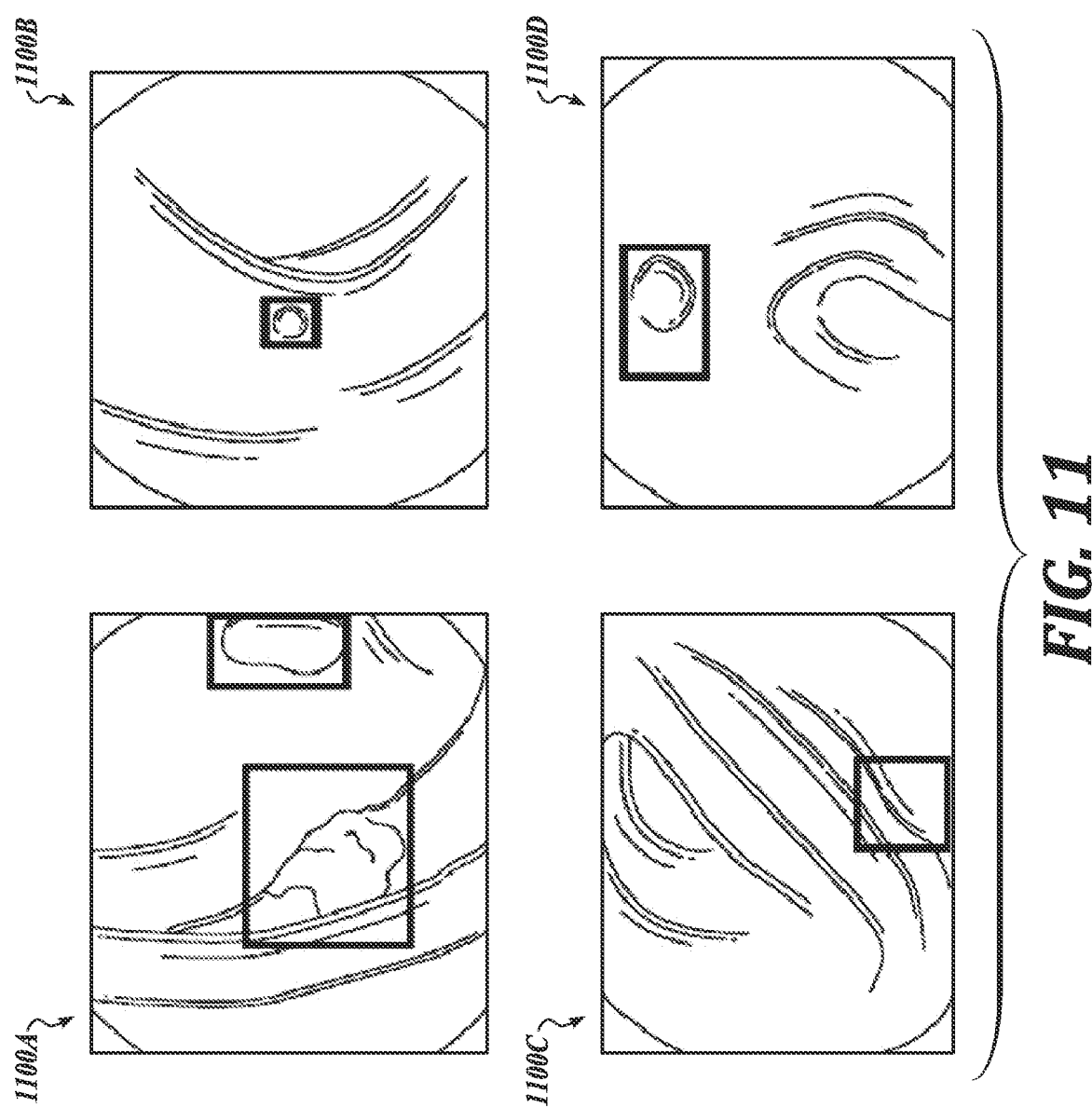
FIG. 11 depicts example images of detections associated with the performance of gastroenterological procedures according to example embodiments of the present disclosure.

FIG. 11 depicts example images 1100A-1100D of detections associated with the performance of video-based positioning and navigation during gastroenterological procedures according to example embodiments of the present disclosure. As discussed, the systems and methods of the present disclosure can provide for improvements in detecting abnormalities (e.g., polyps, lesions, tumors, etc.) and determining more precise locations of abnormalities (e.g., polyps, lesions, tumors, etc.) based on video signal data from an endoscopic device (e.g., standard endoscope, WCE, etc.) during a gastroenterological procedures. For example, according to aspects of the present disclosure, real time processing of a video data stream (e.g., generated by an endoscopic device, etc.) can enable more precise localization, positioning, and navigation of an endoscopic device during a patient procedure, thereby improving polyp detection rates and providing for the generation of visual presentations of procedure data (e.g., detection of abnormalities, position/orientation of abnormalities, etc.). As illustrated in FIG. 11, the systems and methods of the present disclosure can provide for the detection of abnormalities (e.g., polyps, lesions, tumors, etc.) during a gastroenterological procedure.

The example images can be displayed on a secondary presentation system (e.g., secondary presentation system 906 in FIG. 9) or transmitted to a remote system for display as part of a virtual second opinion, either live as the procedure is being conducted or subsequently.

As one example, image 1100A illustrates an example detection of a carcinoma to the lower left of the image 1100A and a polyp to the right side of image 1100A. As another example, image 1100B illustrates an example detection of a small adenomatous polyp near the center of image 1100B. In another example, image 1100C illustrates an example detection of a hyperplastic polyp at the bottom center of image 1100C. As another example, image 1100D illustrates an example detection of a polyp at the top center of image 1100C that was detected even though it was only visible in one or two frames of the video captured during the procedure.

Figure 12:
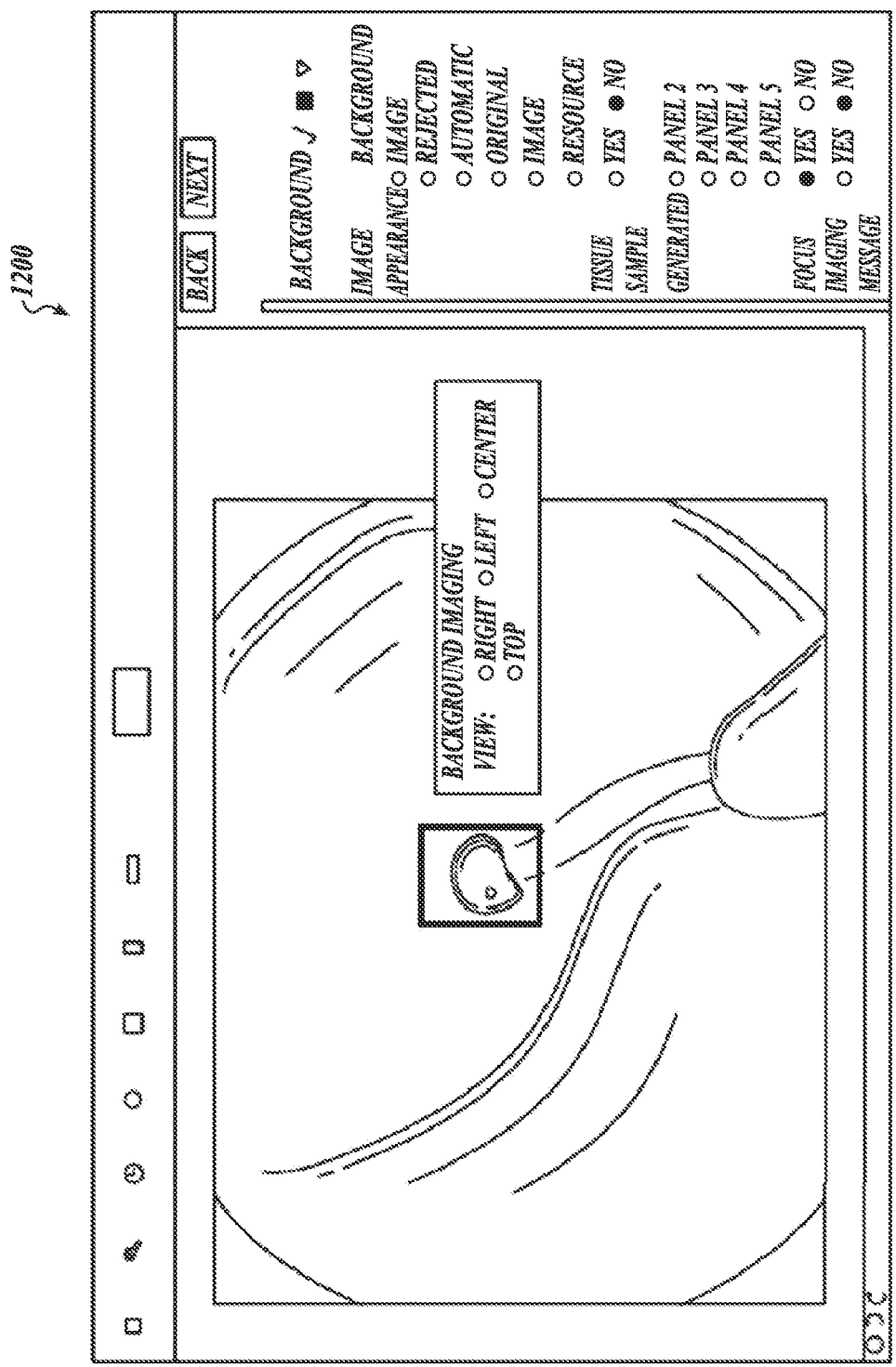
FIG. 12 depicts an example detection output interface associated with the performance of a gastroenterological procedure according to example embodiments of the present disclosure.

FIG. 12 depicts an example detection output interface 1200 associated with the performance of video-based positioning and navigation during a gastroenterological procedure according to example embodiments of the present disclosure. As illustrated in FIG. 12, interface 1200 provides an indication of an abnormality detected during a gastroenterological procedure.

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method for determining coverage in gastroenterological procedures, the method comprising:
   obtaining, by one or more computing devices, a plurality of images captured by an endoscopic device during a gastroenterological procedure for a patient, wherein the plurality of images depict respective portions of an anatomical structure viewed by the endoscopic device;
   processing, by the one or more computing devices using a machine-learned depth estimation model, the plurality of images to obtain a plurality of depth maps respectively for the plurality of images, wherein the depth map obtained for each image describes one or more depths of the respective portions of the anatomical structure from the endoscopic device; and
   determining, by the one or more computing devices using a machine-learned coverage estimation model, a coverage output of the anatomical structure based on the plurality of depth maps, wherein the coverage output indicates an amount of the anatomical structure which has been depicted by the plurality of images.

2. The computer-implemented method of claim 1, further comprising:
   generating, by the one or more computing devices, a visual presentation of the coverage output of the anatomical structure; and
   providing, by the one or more computing devices, the visual presentation of the coverage output of the anatomical structure for use in completion of the gastroenterological procedure or diagnosis of the patient.

3. The computer-implemented method of claim 2, wherein providing, by the one or more computing devices, the visual presentation of the coverage output of the anatomical structure is performed in real-time during the gastroenterological procedure.

4. The computer-implemented method of claim 1, wherein the coverage output indicates a percentage of potentially visible portions of the anatomical structure which were depicted by the plurality of images.

5. The computer-implemented method of claim 1, wherein the machine-learned depth estimation model has been trained in an unsupervised training scheme using a view synthesis loss function that evaluates a reconstructed image that was reconstructed based on a depth map generated by the machine-learned depth estimation model.

6. The computer-implemented method of claim 1, wherein the machine-learned coverage estimation model has been trained in a supervised training scheme using synthetic training data.

7. The computer-implemented method of claim 1, wherein the machine-learned coverage estimation model comprises a first neural network that is configured to generate, for each depth map, a feature map and a second neural network that is configured to generate, from all feature maps, the coverage output for the gastroenterological procedure.

8. The computer-implemented method of claim 7, wherein the first neural network and the second neural network have been separately trained.

9. The computer-implemented method of claim 7, wherein the first neural network was trained to generate, from a depth map, a visibility metric indicative of a set of potentially visible points given a positioning of the endoscopic device.

10. The computer-implemented method of claim 1, wherein the method is performed for each of a plurality of segments of a video of the gastroenterological procedure.

11. The computer-implemented method of claim 1, wherein the anatomical structure comprises a colon and the gastroenterological procedure comprises a colonoscopy.

12. A system for measuring coverage of a gastroenterological procedure, the system comprising:
a computing system comprising one or more processors and a non-transitory computer-readable memory;
wherein the non-transitory computer-readable memory stores instructions that, when executed by the processor, cause the computing system to perform operations, the operations comprising:
obtaining a plurality of images captured by an endoscopic device during a gastroenterological procedure for a patient, wherein the plurality of images depict respective portions of an anatomical structure viewed by the endoscopic device;
processing, using a machine-learned depth estimation model, the plurality of images to obtain a plurality of depth maps respectively for the plurality of images, wherein the depth map obtained for each image describes one or more depths of the respective portions of the anatomical structure from the endoscopic device; and
determining, using a machine-learned coverage estimation model, a coverage output of the anatomical structure based on the plurality of depth maps, wherein the coverage output indicates an amount of the anatomical structure which has been depicted by the plurality of images.

13. The system of claim 12, the operations further comprising:
generating a visual presentation of the coverage output of the anatomical structure; and
providing the visual presentation of the coverage output of the anatomical structure for use in completion of the gastroenterological procedure or diagnosis of the patient.

14. The system of claim 12, wherein providing the visual presentation of the coverage output of the anatomical structure is performed in real-time during the gastroenterological procedure.

15. The system of claim 12, wherein the coverage output indicates a percentage of potentially visible portions of the anatomical structure which were depicted by the plurality of images.

16. The system of claim 12, wherein the machine-learned depth estimation model has been trained in an unsupervised training scheme using a view synthesis loss function that evaluates a reconstructed image that was reconstructed based on a depth map generated by the machine-learned depth estimation model.

17. The system of claim 12, wherein the machine-learned coverage estimation model has been trained in a supervised training scheme using synthetic training data.

18. The system of claim 12, wherein the machine-learned coverage estimation model comprises a first neural network that is configured to generate, for each depth map, a feature map and a second neural network that is configured to generate, from all feature maps, the coverage output for the gastroenterological procedure.

19. A non-transitory computer-readable medium storing instruction that, when executed by one or more computing devices, cause the one or more computing devices to perform operations, the operations comprising:
obtaining a plurality of images captured by an endoscopic device during a gastroenterological procedure for a patient, wherein the plurality of images depict respective portions of an anatomical structure viewed by the endoscopic device;
processing, using a machine-learned depth estimation model, the plurality of images to obtain a plurality of depth maps respectively for the plurality of images, wherein the depth map obtained for each image describes one or more depths of the respective portions of the anatomical structure from the endoscopic device;
determining, using a machine-learned coverage estimation model, a coverage output of the anatomical structure based on the plurality of depth maps, wherein the coverage output indicates an amount of the anatomical structure which has been depicted by the plurality of images.

20. The non-transitory computer-readable medium of claim 19, wherein the operations further comprise:
generating a visual presentation of the coverage output of the anatomical structure; and
providing the visual presentation of the coverage output of the anatomical structure for use in completion of the gastroenterological procedure or diagnosis of the patient.

* * * * *